(12) United States Patent
Moulder et al.

(10) Patent No.: US 7,197,360 B1
(45) Date of Patent: Mar. 27, 2007

(54) METHODS AND SYSTEMS FOR USING AN INDUCTOR TO INCREASE CAPACITOR REFORMATION EFFICIENCY IN AN IMPLANTABLE CARDIAC DEVICE (ICD)

(75) Inventors: J. Christopher Moulder, Encino, CA (US); Joseph Beauvais, Stevenson Ranch, CA (US); George I. Isaac, Port Hueneme, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 260 days.

(21) Appl. No.: 11/035,348

(22) Filed: Jan. 12, 2005

(51) Int. Cl.
*A61N 1/00* (2006.01)
(52) U.S. Cl. .............................................. 607/5; 607/7
(58) Field of Classification Search .................... 607/5, 607/7, 29, 34
See application file for complete search history.

(56) References Cited

U.S. PATENT DOCUMENTS

| | | | |
|---|---|---|---|
| 4,712,555 A | 12/1987 | Thornander et al. | 128/419 PG |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 5,450,308 A * | 9/1995 | Tai | 363/57 |
| 5,792,188 A | 8/1998 | Starkweather et al. | 607/5 |
| 5,861,006 A | 1/1999 | Kroll | 607/5 |
| 5,899,923 A | 5/1999 | Kroll et al. | 607/5 |
| 6,283,985 B1 | 9/2001 | Harguth et al. | 607/1 |
| 6,706,059 B2 | 3/2004 | Harguth et al. | 607/1 |
| 2001/0047190 A1 | 11/2001 | Harguth et al. | 607/1 |
| 2002/0095186 A1 | 7/2002 | Harguth et al. | 607/5 |
| 2004/0036448 A1 | 2/2004 | Gan et al. | 320/127 |
| 2004/0051504 A1 | 3/2004 | Syracuse et al. | 320/127 |
| 2004/0098058 A1 | 5/2004 | Harguth et al. | 607/11 |

FOREIGN PATENT DOCUMENTS

| | | |
|---|---|---|
| EP | 1 312 390 A2 | 5/2003 |
| WO | WO 03/045497 A2 | 6/2003 |

* cited by examiner

*Primary Examiner*—Robert E. Pezzuto
*Assistant Examiner*—Brian T. Gedeon

(57) ABSTRACT

Methods and systems for increasing capacitor reformation efficiency in an implantable cardiac device (ICD) are presented. In one embodiment, a method and system provide for: (1) fully charging a first capacitor, (2) transferring energy from the first capacitor to an inductor, (3) transferring energy from the inductor to the second capacitor, and (4) completing charging of the second capacitor. In another embodiment, a method and system provide for: (1) fully charging a first capacitor, (2) sharing energy from the first capacitor with a second capacitor, and (3) completing charging of the second capacitor. In yet another embodiment, a method and system provide for: (1) fully charging a first capacitor, (2) sharing energy from the first capacitor with a second capacitor, (3) transferring remaining energy from the first capacitor to an inductor, (4) transferring energy from the inductor to the second capacitor, and (5) completing charging of the second capacitor.

20 Claims, 18 Drawing Sheets

METHODS AND SYSTEMS FOR USING AN INDUCTOR TO INCREASE CAPACITOR REFORMATION EFFICIENCY IN AN IMPLANTABLE CARDIAC DEVICE (ICD)

CROSS-REFERENCE TO RELATED APPLICATIONS

This application is related to copending U.S. patent application Ser. No. 11/035,347, titled "Methods and Systems for increased CAPACITOR reformation efficiency in an Implantable Cardiac Device (ICD)", filed concurrently herewith.

FIELD OF THE INVENTION

The present invention relates generally to implantable cardiac devices (ICDs) and, more particularly, to methods and systems for reformation of ICD high voltage capacitors.

BACKGROUND

Typical ICDs include high voltage capacitors for delivering defibrillation shocks to a patient. In order for ICDs to maintain fast charge times for defibrillation shocks, the high voltage capacitors must be periodically "formed." Forming the capacitors requires charging them to at least full energy (e.g., 36 Joules) once every several months (e.g., every three months). At battery mid-life, the capacitors may be formed more frequently (e.g., every month) in order to manage an ICD battery voltage delay phenomenon.

Capacitor reformation reduces the longevity of the ICD battery. Furthermore, after capacitor reformation, the charge on the high voltage capacitors is essentially wasted because the charge is not used for a defibrillation shock or for any other purpose.

What is needed, therefore, are methods and systems for decreasing the amount of energy used for ICD capacitor reformation, thereby increasing the longevity of the ICD battery.

SUMMARY

Methods and systems for increasing capacitor reformation efficiency in an ICD are presented. The methods and systems decrease the amount of energy used for capacitor reformation, thereby increasing the longevity of the ICD battery.

In one embodiment, a method and system increase capacitor reformation efficiency in an ICD by transferring energy from a first capacitor to a second capacitor through an inductor to at least partially charge the second capacitor. In another embodiment, a method and system increase capacitor reformation efficiency in an ICD by sharing energy from a first capacitor with a second capacitor, and by transferring the remaining energy from the first capacitor to the second capacitor through an inductor to at least partially charge the second capacitor.

Further features and advantages of the methods and systems presented herein, as well as the structure and operation of various example methods and systems, are described in detail below with reference to the accompanying drawings.

BRIEF DESCRIPTION OF THE DRAWINGS/FIGURES

The accompanying drawings, which are incorporated herein and form part of the specification, illustrate the methods and systems for increased capacitor reformation efficiency presented herein. Together with the description, the drawings further serve to explain the principles of and to enable a person skilled in the relevant art(s) to make and use the methods and systems presented herein. In the drawings, like reference numbers indicate identical or functionally similar elements, and the drawing in which an element first appears is typically indicated by the leftmost digit(s) in the corresponding reference number.

Figure 15:
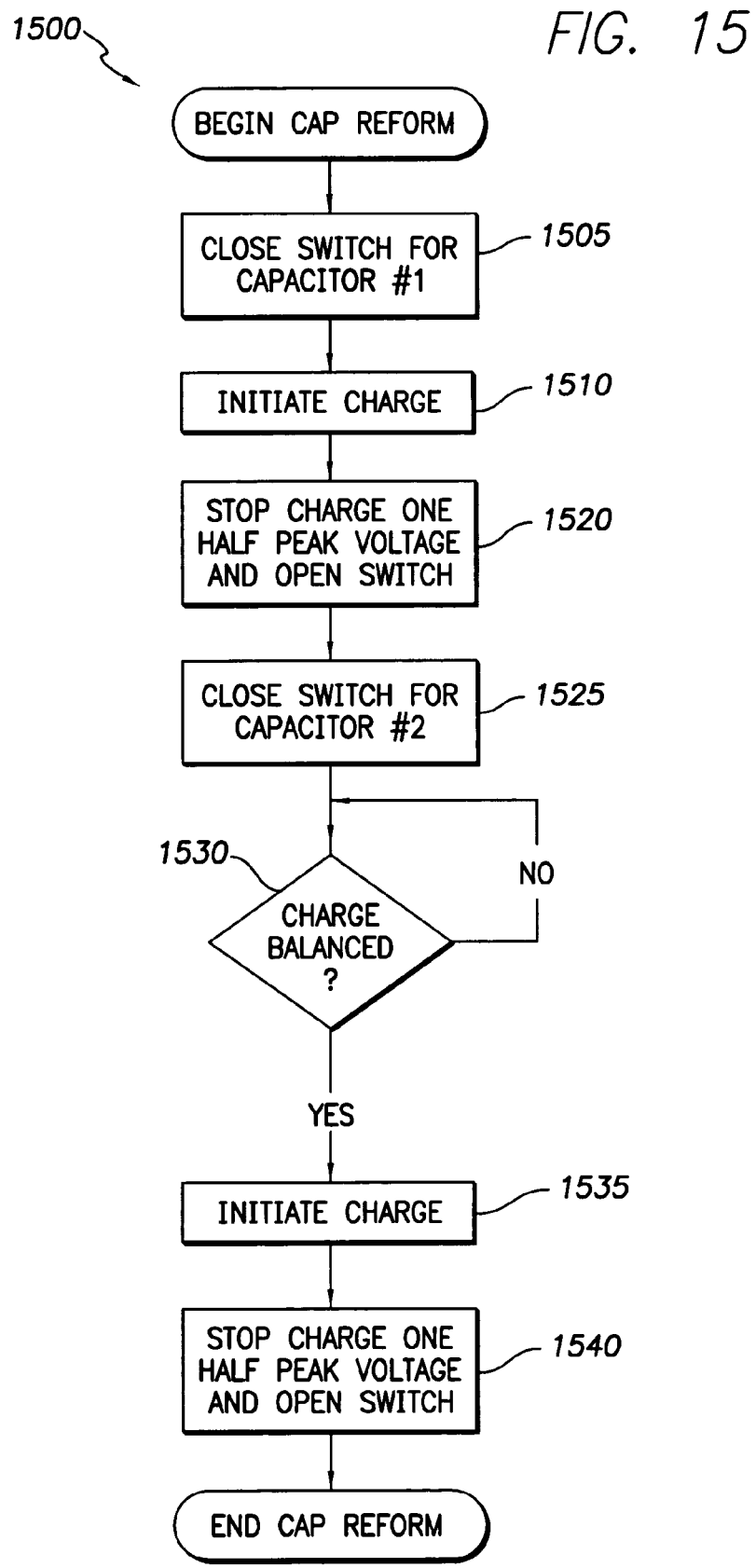

FIG. 15. shows a process flowchart providing steps for sharing energy between two capacitors to increase capacitor reformation efficiency in an ICD.

Figure 16:
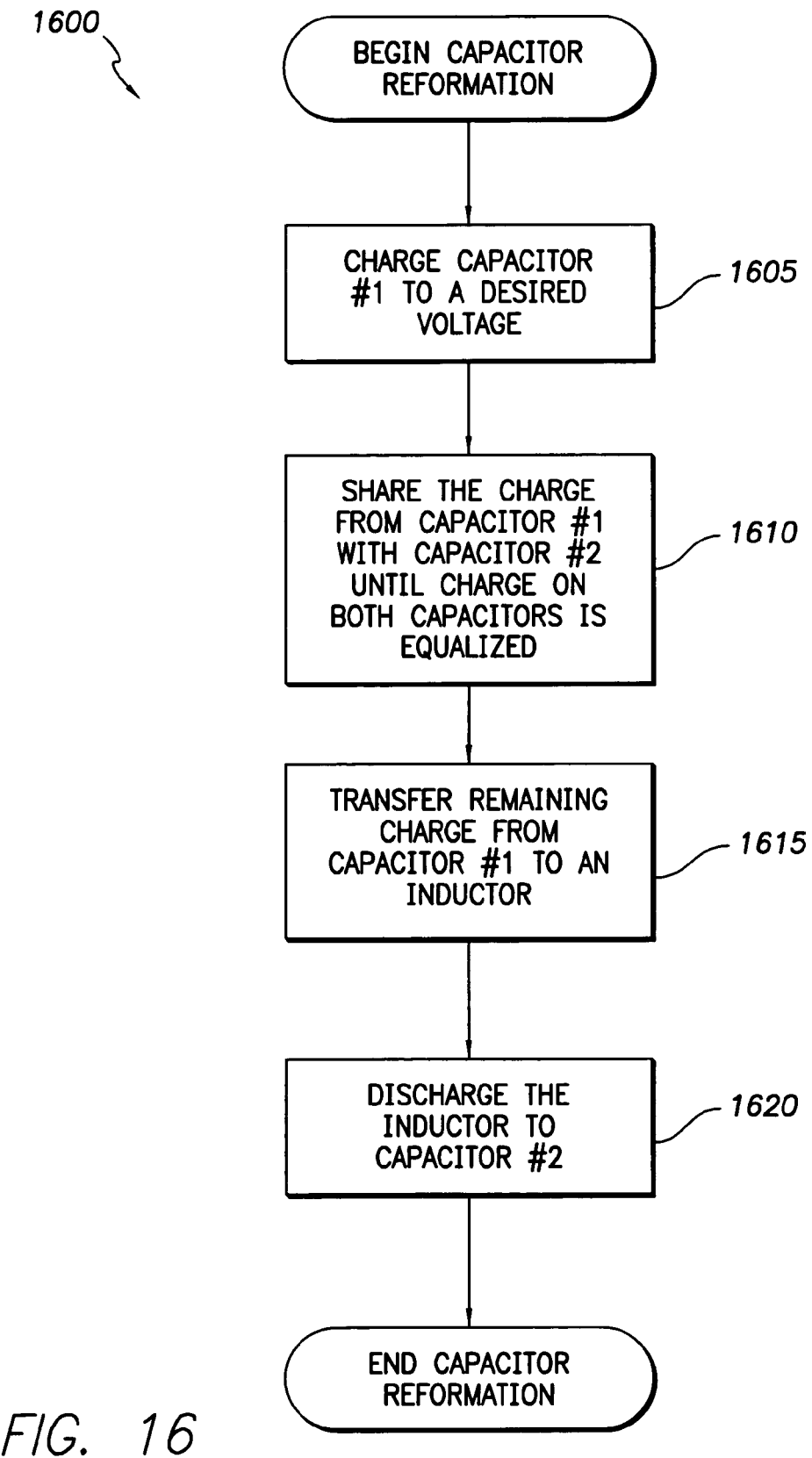

FIG. 16 shows a high level process flowchart providing steps for sharing and transferring energy between two capacitors to increase capacitor reformation efficiency in an ICD.

Figure 17:
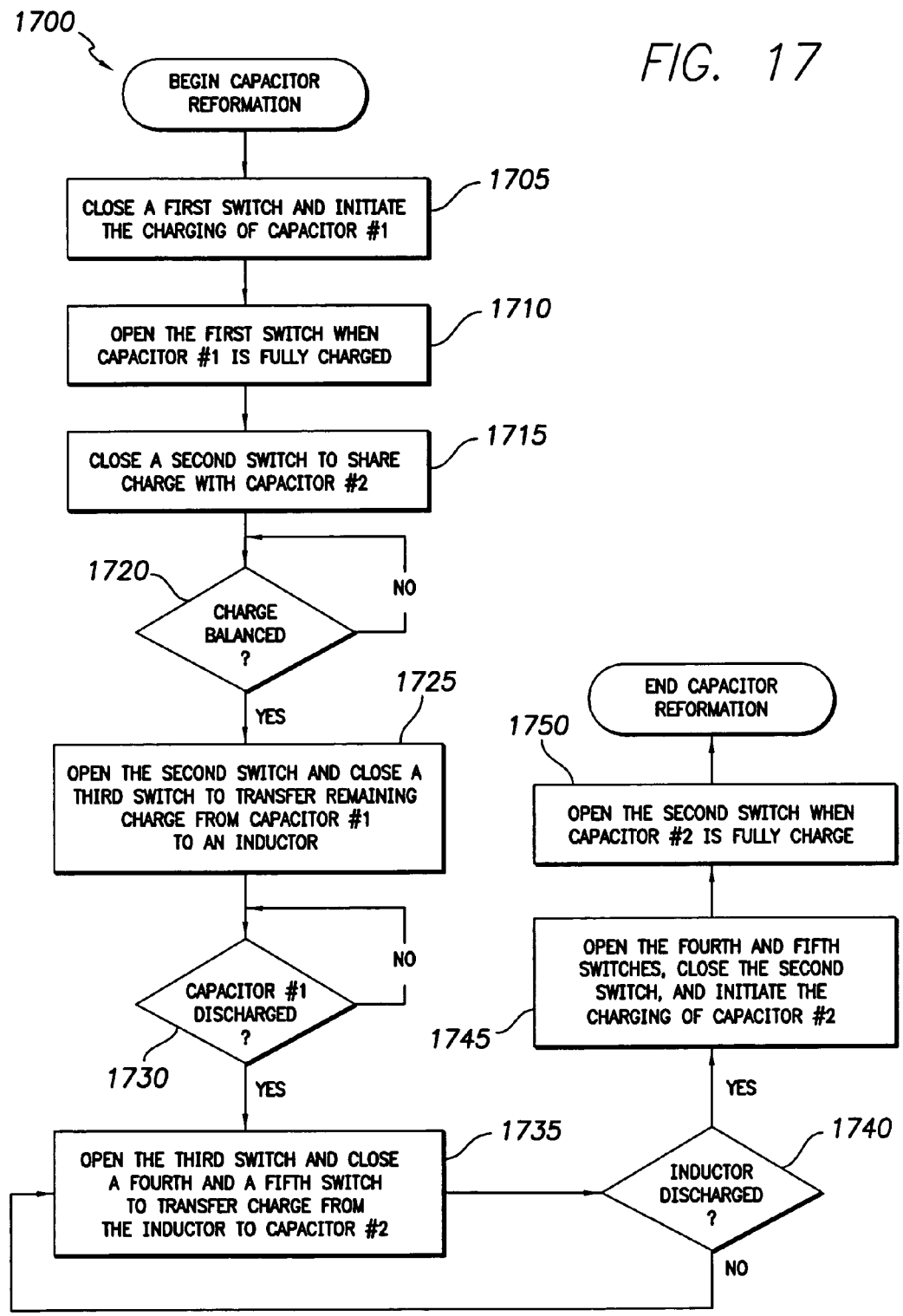

FIG. 17 shows a detailed process flowchart providing steps for sharing and transferring energy between two capacitors to increase capacitor reformation efficiency in an ICD.

Figure 18:
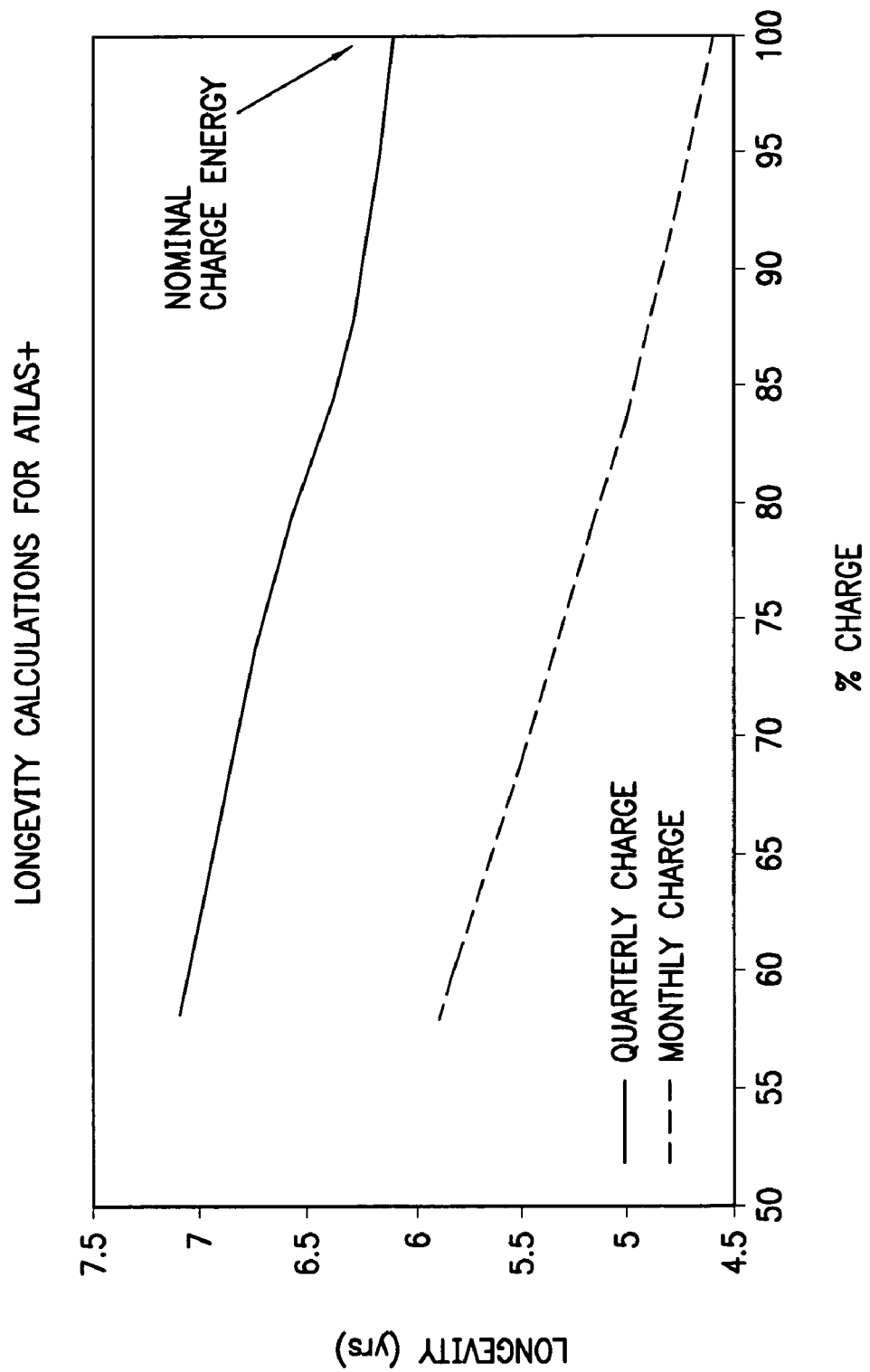

FIG. 18 shows a plot of the increased longevity of an example ICD as a function of the amount of charge required for periodic capacitor reformation.

DETAILED DESCRIPTION

Overview

The following detailed description of the methods and systems for increased capacitor reformation efficiency in an ICD refers to the accompanying drawings that illustrate example embodiments. Other embodiments are possible, and modifications may be made to the embodiments within the spirit and scope of the methods and systems presented herein. Therefore, the following detailed description is not meant to limit the methods and systems described herein but rather, their scope is defined by the appended claims.

It would be apparent to one of skill in the art that the methods and systems for increased capacitor reformation efficiency in an ICD, as described below, may be implemented in many different embodiments of hardware, software, firmware, and/or the entities illustrated in the figures. Any actual software and/or hardware described herein is not limiting of the methods and systems presented herein. Thus, the operation and behavior of the methods and systems presented will be described with the understanding that modifications and variations of the embodiments are possible, given the level of detail presented herein.

Figure 1:
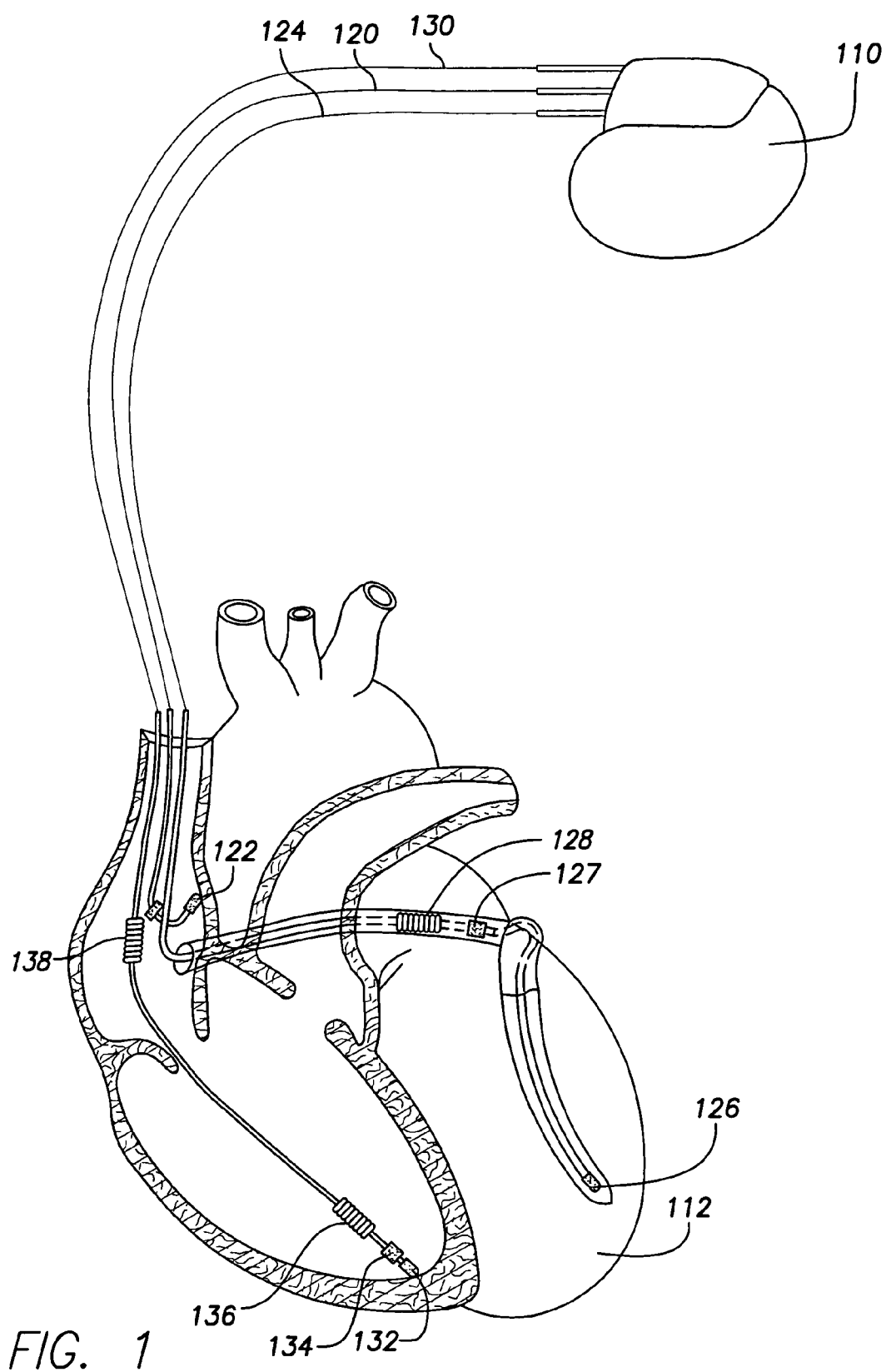
FIG. 1 is a simplified diagram illustrating an example ICD in electrical communication with a patient's heart by means of three leads suitable for delivering multi-chamber stimulation and pacing therapy.
Figure 2:
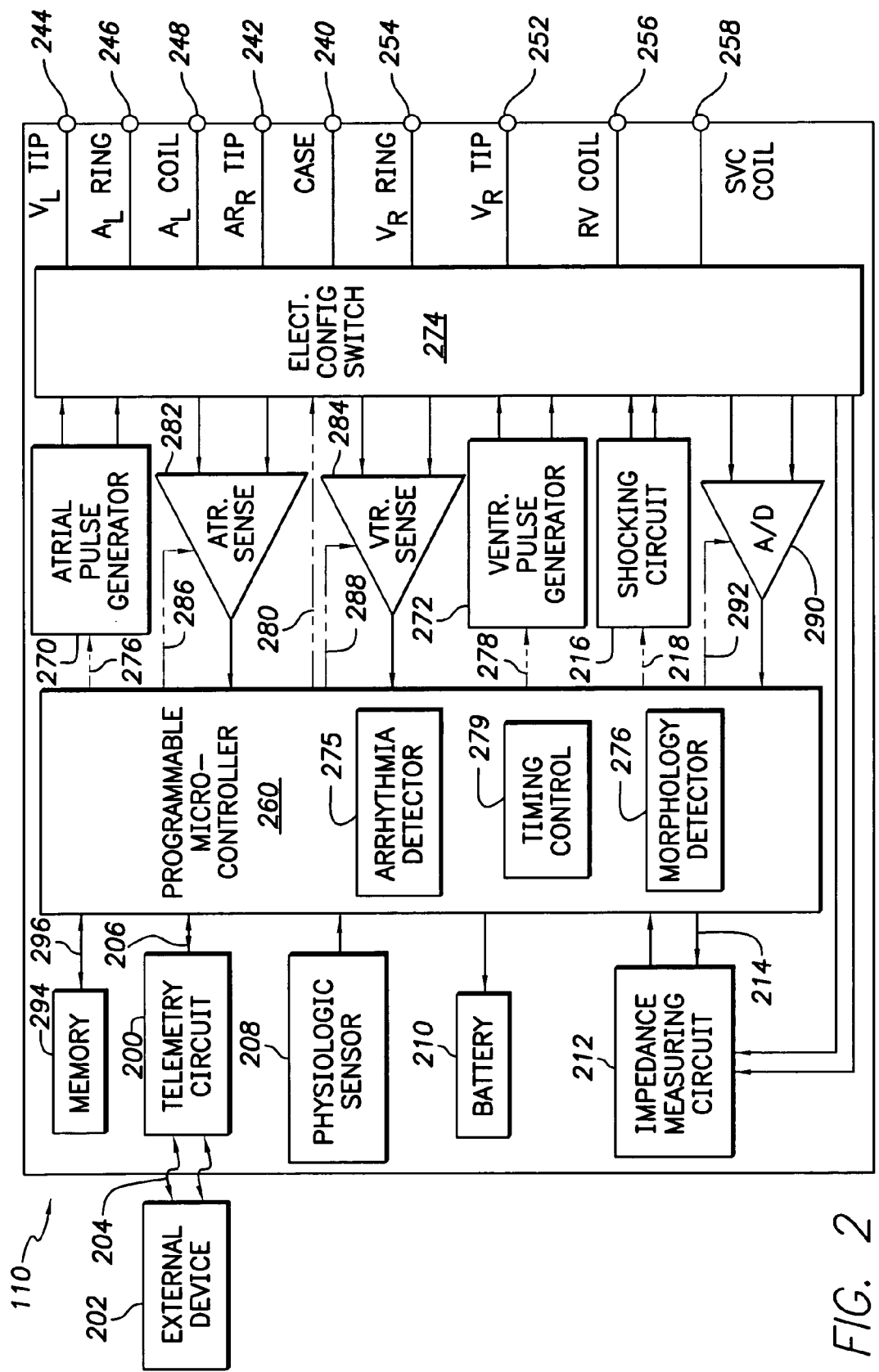
FIG. 2 is a functional block diagram of an example ICD that can provide cardioversion, defibrillation, and pacing stimulation in four chambers of a heart.

Before describing example methods and systems for increased capacitor reformation efficiency in detail, it is helpful to describe an example environment in which they may be implemented. The methods and systems for increased capacitor reformation efficiency are particularly useful in the environment of an ICD. An ICD is a medical device that is implanted in a patient to monitor electrical activity of a heart and to deliver appropriate electrical therapy, for example, pacing pulses, cardioverting and defibrillation pulses, as required. ICDs include, for example, pacemakers, cardioverters, defibrillators, implantable cardioverter defibrillators, and the like. The term "implantable cardiac defibrillator" or simply "ICD" is used herein to refer to any implantable cardiac device. FIGS. 1 and 2 illustrate such an environment including the methods and systems.

Exemplary ICD in Electrical Communication with a Patient's Heart

FIG. 1 illustrates an exemplary ICD 110 in electrical communication with a patient's heart 112 by way of three leads, 120, 124 and 130, suitable for delivering multi-chamber stimulation and pacing therapy. To sense atrial cardiac signals and to provide right atrial chamber stimulation therapy, ICD 110 is coupled to implantable right atrial lead 120 having at least an atrial tip electrode 122, which typically is implanted in the patient's right atrial appendage.

To sense left atrial and ventricular cardiac signals and to provide left-chamber pacing therapy, ICD 110 is coupled to "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 124 is designed to receive atrial and ventricular cardiac signals and to deliver left ventricular pacing therapy using at least a left ventricular tip electrode 126, left atrial pacing therapy using at least a left atrial ring electrode 127, and shocking therapy using at least a left atrial coil electrode 128.

ICD 110 is also shown in electrical communication with the patient's heart 112 by way of implantable right ventricular lead 130 having, in this embodiment, a right ventricular tip electrode 132, a right ventricular ring electrode 134, a right ventricular (RV) coil electrode 136, and a superior vena cava (SVC) coil electrode 138. Typically, right ventricular lead 130 is transvenously inserted into heart 112 so as to place right ventricular tip electrode 132 in the right ventricular apex so that RV coil electrode 136 will be positioned in the right ventricle and SVC coil electrode 138 will be positioned in the SVC. Accordingly, right ventricular lead 130 is capable of receiving cardiac signals and delivering stimulation in the form of pacing and shock therapy to the right ventricle.

Functional Elements of an Exemplary ICD

FIG. 2 shows a simplified block diagram of ICD 110, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

At the core of ICD 110 is a programmable microcontroller 260, which controls the various modes of stimulation therapy. As is well known in the art, microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 260 includes the ability to process or monitor input signals (data) as controlled by a program code stored in a designated block of memory.

The details of the design of microcontroller 260 are not critical to the methods and systems for increased capacitor reformation efficiency described herein. Rather, any suitable microcontroller 260 can be used to carry out the functions described herein. The use of microprocessor-based control circuits for performing timing and data analysis functions are well known in the art.

Representative types of control circuitry that may be used include the microprocessor-based control system of U.S. Pat. No. 4,940,052 (Mann et. al.) and the state-machines of U.S. Pat. No. 4,712,555 (Thornander et al.) and U.S. Pat. No. 4,944,298 (Sholder). For a more detailed description of the various timing intervals used within the ICD's and their inter-relationship, see U.S. Pat. No. 4,788,980 (Mann et. al.). The '052, '555, '298 and '980 patents are incorporated herein by reference.

As shown in FIG. 2, microcontroller 260 controls an atrial pulse generator, a ventricular pulse generator, and atrial and ventricular sensing circuits, to trigger or inhibit delivery of pacing stimulation pulses, as is well known in the art. When ICD 110 operates as a cardioverter, pacer or defibrillator, microcontroller 260 further controls a shocking circuit capable of generating shocking pulses of low (up to about 0.5 Joules), moderate (about 0.5–10 Joules), or high energy (about 11 to 40 Joules). Microcontroller 260 can also control an analog-to-digital (A/D) data acquisition system, configured to acquire intracardiac electrogram signals and convert the raw analog data into a digital signal.

As shown in FIG. 2, microcontroller 260 can include arrhythmia detection and morphology detection circuitry to recognize and classify arrhythmia in order to deliver appropriate therapy to a patient. Microcontroller 260 can further include timing control circuitry to control pacing parameters (e.g., the timing of stimulation pulses) and monitor the timing of refractory periods, PVARP intervals, noise detection windows, evoked response windows, alert intervals, marker channel timing, etc., which are well known in the art.

In the example of FIG. 2, ICD 110 further includes a plurality of switches for connecting desired electrodes to appropriate I/O circuits in response to a control signal from microcontroller 260, as is known in the art. ICD 110 further includes a memory, which stores and modifies, as required, the programmable operating parameters used by microcontroller 260 to customize the operation of ICD 110 to suit the needs of a particular patient. Also shown in FIG. 2 as part of ICD 110 is a telemetry circuit for communicating intracardiac electrograms and status information relating to the operation of ICD 110 to an external device through an established communications link.

As shown in FIG. 2, ICD 110 includes a battery 210. Battery 210 provides operating power to a load that includes all of the circuits shown in FIG. 2. Battery 210 must be capable of operating at low current drains for long periods of time, and must also be capable of providing high-current pulses (e.g., tens of milliamperes to several amperes) for charging the shocking capacitors to deliver electrical therapy (e.g., defibrillation), for periodic reformation of the shocking capacitors, and for exercise of battery 210.

Electrolytic capacitors are typically used in ICDs, such as ICD 110 shown in FIGS. 1 and 2, because they have the most nearly ideal properties in terms of size, reliability, delivered energy and ability to withstand relatively high voltage. Typically, these capacitors can be aluminum electrolytic capacitors having aluminum foil plates or tantalum having tantalum pellets. Many ICDs usually contain two electrolytic capacitors configured in a series arrangement for shock delivery. For example, two 400 V rated capacitors arranged in series can be used to deliver an 800 V shock.

It is important that the anode used in these capacitors maintains a high capacitance with the lowest possible leakage current. The term "leakage current" refers to the current passing from the cathode plate through an electrolyte and across the anodic oxide dielectric into the anode. Under conventional anode preparation techniques, a barrier oxide layer is formed onto one or both surfaces of a metal. The oxide film must be sufficiently thick to support the intended use voltage for shock delivery (referred to hereinafter as the "nominal voltage"). This oxide film acts as a dielectric layer for the capacitor, and constitutes a barrier to the flow of current between the electrolyte and the metal, thereby providing a high resistance to leakage current passing between the anode and cathode. However, a small amount of current, the leakage current, still passes through the barrier oxide layer due to intrinsic defects in the crystalline oxide. A high leakage current can result in the poor performance and reliability of an electrolytic capacitor. In particular, a high leakage current results in a greater amount of charge lost internally to the capacitor once it has been charged.

Both cardioversion and defibrillation require that a high voltage shock be delivered to the heart. Because of the limited energy available from the ICD's battery, such as battery 210 shown in FIG. 2, it is impractical to continuously maintain the capacitors at a full voltage charge. Instead, to conserve energy, the capacitors are typically only charged after detection of an arrhythmia in preparation for delivering a shock to the heart.

To shorten the time between arrhythmia onset and therapy, pulse discharge capacitors, such as those in ICDs, are required to charge quickly after protracted storage in the discharged state. However, leaving the capacitors in an uncharged state leads to degradation of the oxide on the capacitors over time. Instability of the oxide in the liquid electrolyte results in degradation over time of the charging efficiency of the capacitor. For this reason, ICDs containing electrolytic capacitors typically also include capacitor maintenance software to periodically reform the oxide on the electrolytic capacitors. The periodic reformation process serves to replenish the oxide and reduce the leakage current of the electrolytic capacitors. This, in turn, reduces charge time of the capacitors the first time that they are needed for therapeutic use after an extended period of non-use.

Conventionally, the reformation process consists of charging the electrolytic capacitors to the device's nominal voltage and then allowing the charge to dissipate.

A capacitor maintenance interval is generally established with a range of 1–6 months. When the capacitor maintenance interval times out, the device performs capacitor maintenance. Typically, capacitor maintenance consists of the ICD's software requesting charging of the capacitors to the device's nominal voltage. After the capacitor maintenance charge to the device's nominal voltage is completed, the capacitor maintenance interval is restarted. The charge on the capacitors is allowed to dissipate by leaking through some parasitic discharge path. Alternatively, the ICDs may be programmed to dump the capacitor charge into an internal ("dummy") load after a specified time interval.

While capacitor reformation is necessary for optimal ICD performance, it is desirable to reduce the amount of energy used in reformation so that ICD battery life can be extended.

Example Systems for Increasing Capacitor Reformation Efficiency in an ICD

Example systems for increasing capacitor reformation efficiency in an ICD are described below. These example systems increase capacitor reformation efficiency by decreasing the amount of energy required to form the capacitors, thereby increasing the longevity of the ICD. One example system is configured to transfer energy from one high voltage capacitor to another high voltage capacitor using an inductor. Another example system is configured to share energy from one high voltage capacitor with another high voltage capacitor until the charge on the two capacitors is balanced/equalized. Thus, both systems are configured to at least partially charge one capacitor with energy from another capacitor so that less energy is required to reform both capacitors. These example systems are described below in more detail.

Figure 3:
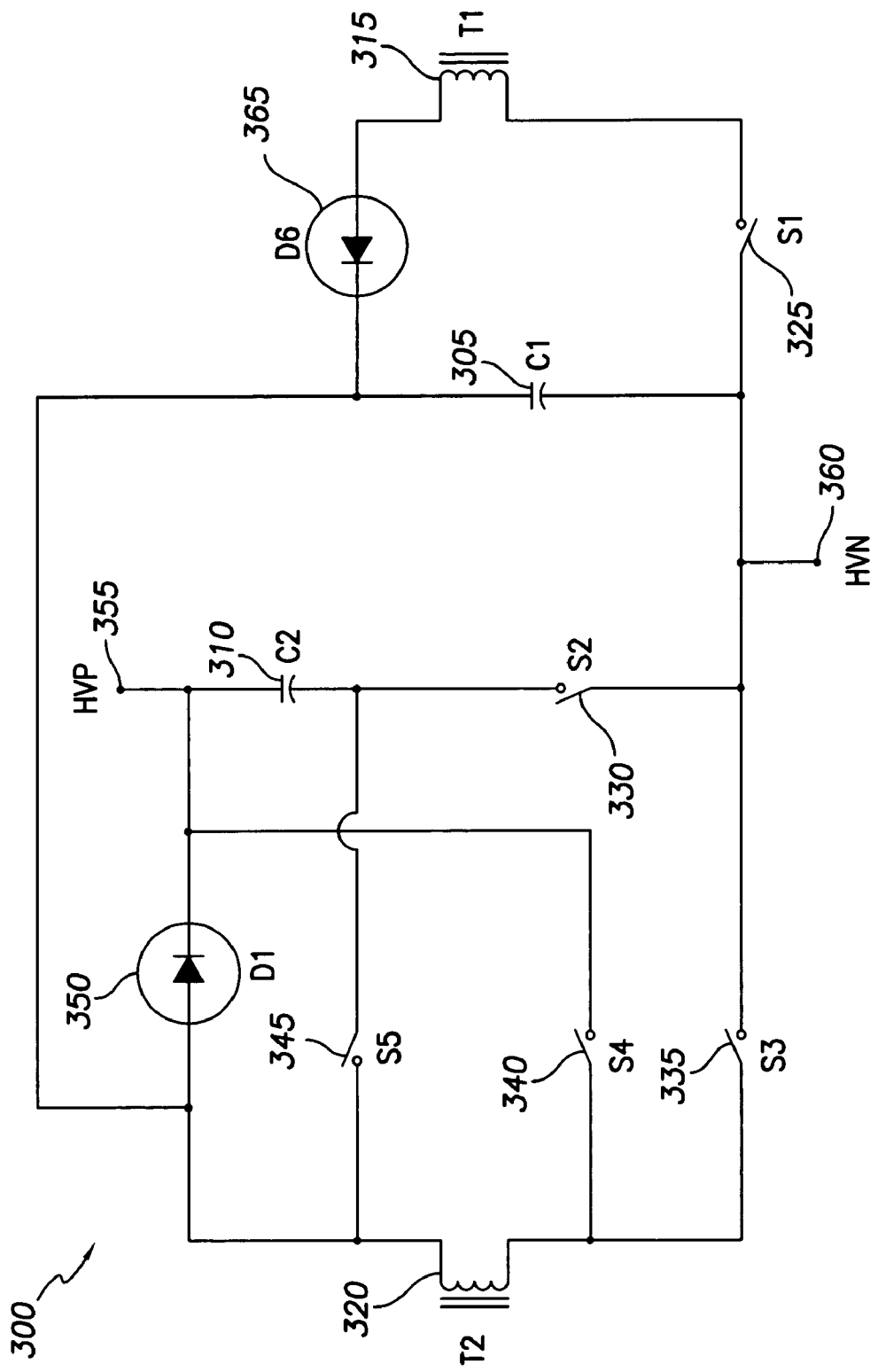
FIGS. 3–7 illustrate an example system for transferring energy from one capacitor to another capacitor through an inductor to increase capacitor reformation efficiency in an ICD.

FIGS. 3–6 illustrate an example system 300 for transferring energy from one high voltage capacitor to another high voltage capacitor using an inductor to increase capacitor reformation efficiency in an ICD. As shown in FIG. 3, system 300 includes first and second capacitors 305 and 310, and first and second high voltage transformers (i.e. transformers secondary windings) 315 and 320. System 300 further includes a first switch 325, a second switch 330, a third switch 335, a fourth switch 340, and a fifth switch 345, in addition to a diode 350 and a diode 365.

As shown in FIG. 3, first switch 325 is coupled between first high voltage transformer 315 and a cathode of first capacitor 305, while second switch 330 is coupled between a cathode of second capacitor 310 and the cathode of first capacitor 305. Third switch 335 is coupled between second switch 330 and second high voltage transformer 320. Fourth switch 340 is coupled between second high voltage transformer 320 and an anode of second capacitor 310, and fifth switch 345 is coupled between second high voltage transformer 320 and the cathode of second capacitor 310. Diode 350 has an anode coupled to first high voltage transformer 315, second high voltage transformer 320, and the anode of first capacitor 305. Diode 350 further has a cathode coupled to fourth switch 340 and the anode of second capacitor 310. The anode of second capacitor 310 is coupled to a positive high voltage bus 355, and the cathode of first capacitor 305 is coupled to a negative high voltage bus 360. Diode 365 is coupled between anode of first capacitor 305 and first high voltage transformer 315.

Figure 4:
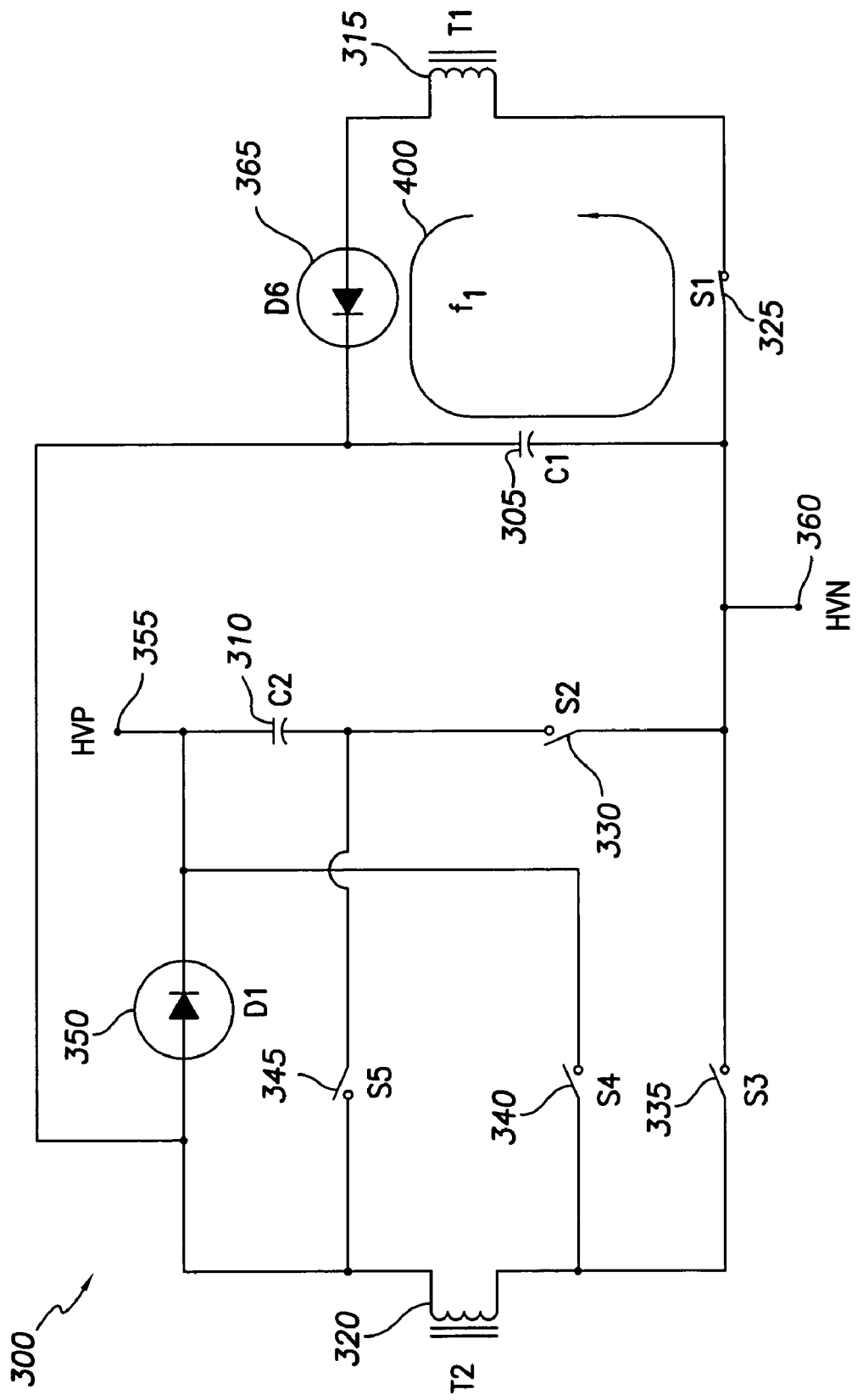

FIG. 4 illustrates a current path 400 that exists when first switch 325 is closed and second switch 330, third switch 335, fourth switch 340, and fifth switch 345 are open. When the switches of system 300 are configured as shown in FIG. 4, first high voltage transformer 315 charges first capacitor 305 to a desired voltage.

Figure 5A:
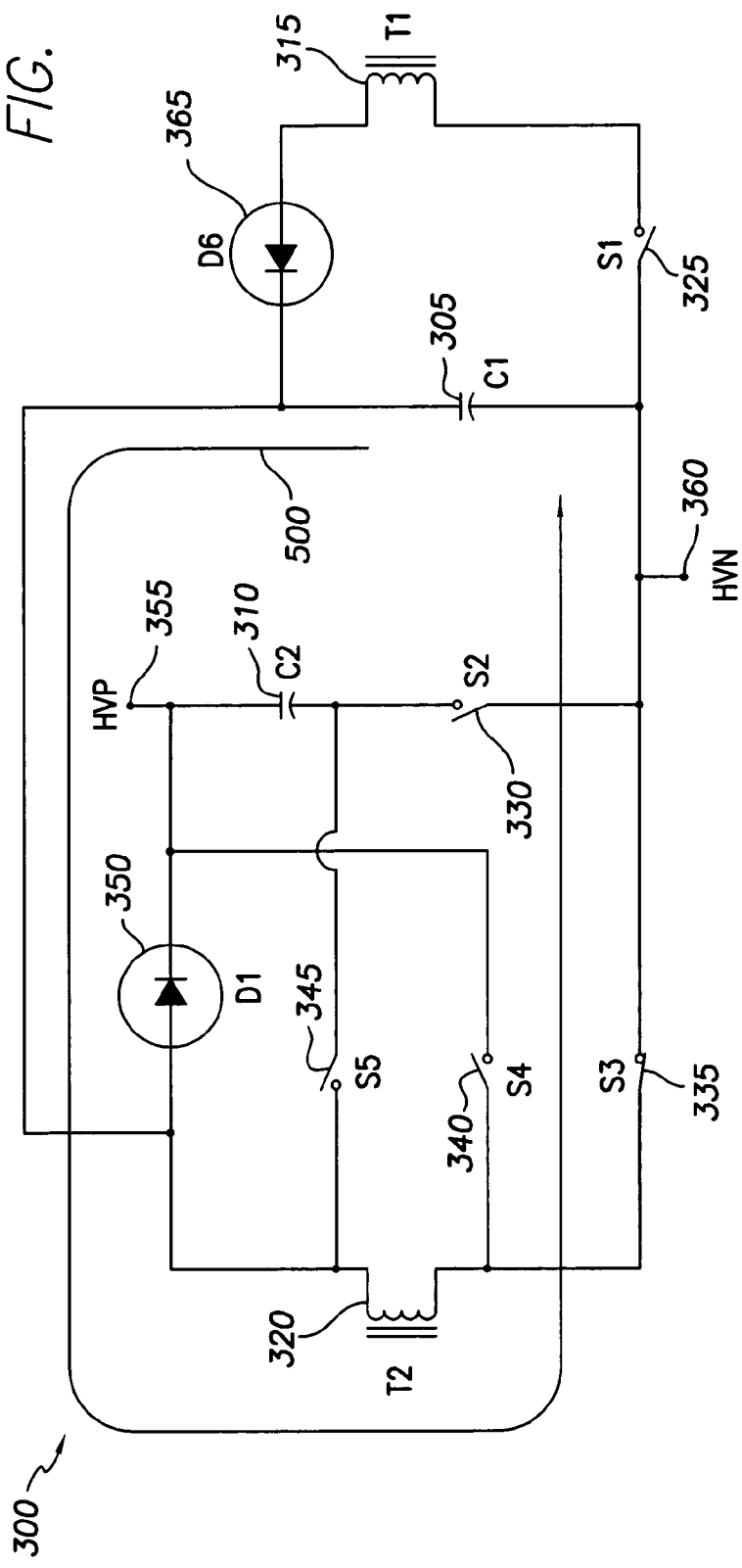
Figure 5B:
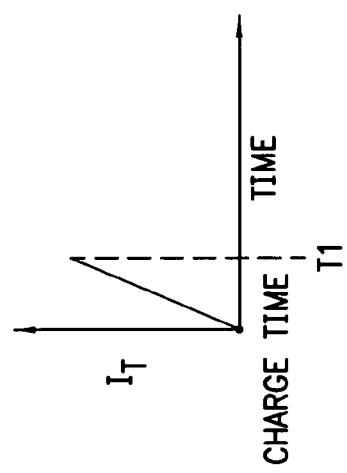

FIG. 5A illustrates a current path 500 that exists when third switch 335 is closed, and first switch 325, second switch 330, fourth switch 340, and fifth switch 345 are open. In FIG. 5A, current flows from first capacitor 305 and is stored in second high voltage transformer 320, which is serving as an inductor. FIG. 5B shows a plot of the amount of current flow in second high voltage transformer 320 versus time. The amount of energy stored in second high voltage transformer 320 increases with time until a specified energy time, T1. After time T1, third switch 335 is open.

Figure 6A:
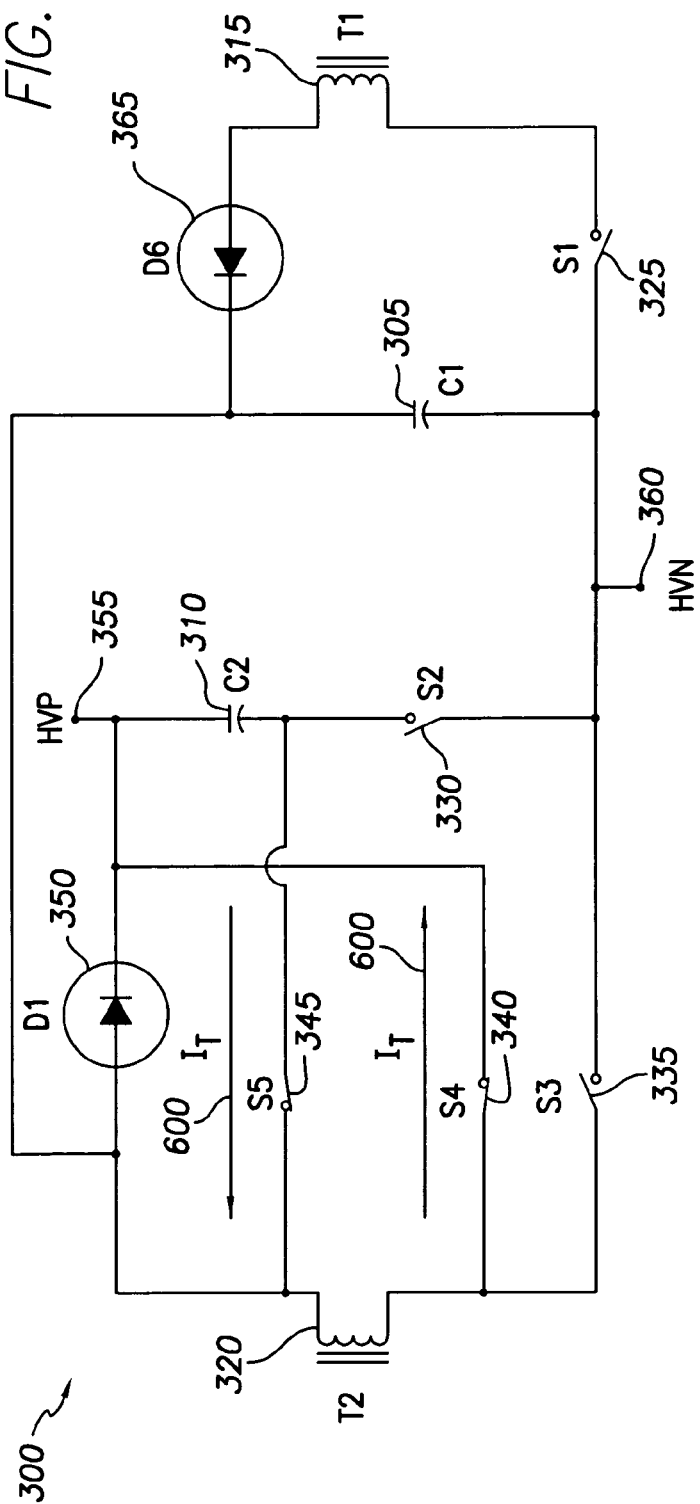
Figure 6B:
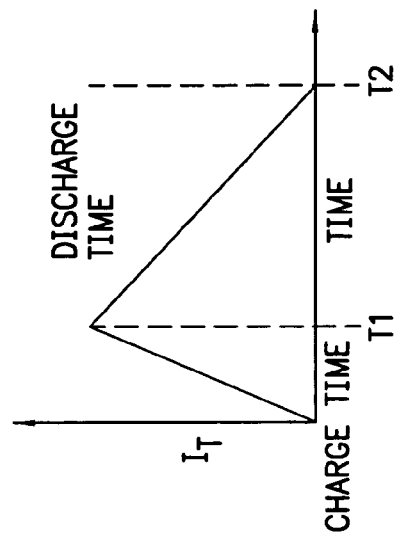

FIG. 6A illustrates a current path 600 that exists when fourth switch 340 and fifth switch 345 are closed, and first switch 325, second switch 330, and third switch 335 are open. When the switches of system 300 are configured as shown in FIG. 6A, current flows from second high voltage transformer 320 and charges second capacitor 310. FIG. 6B shows a plot of an amount of current flow in second high voltage transformer 320 versus time. The amount of current flow in second high voltage transformer 320 decreases with time from time T1 to a specified discharge time, T2. After time T2, fourth switch 340 and fifth switch 345 are open.

Figure 7:
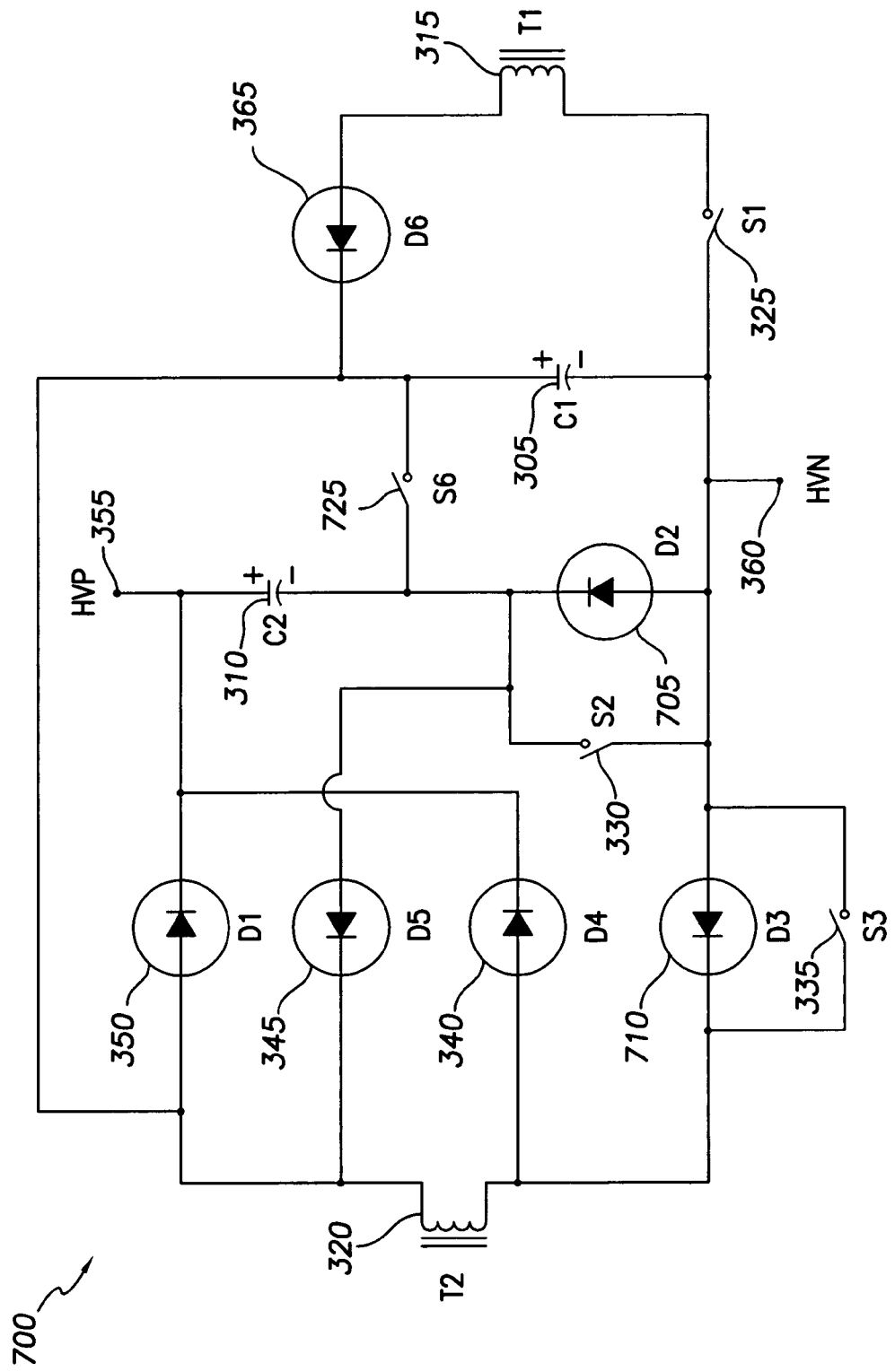

The energy transfers shown in FIGS. 5A and 6A may be repeated as necessary until all of the charge stored on first capacitor 305 is transferred to second capacitor 310. Because the energy transfer from first capacitor 305 to second capacitor 310 through second high voltage transformer 320 is not ideal (i.e., there are parasitic and other losses in the circuit), the energy from first capacitor 305 only partially charges second capacitor 310. FIG. 7 illustrates an example system 700 for transferring energy from first capacitor 305 to second capacitor 310 using second high voltage transformer 320 as an inductor, and for completing the charging of second capacitor 310 from partially to fully charged.

System 700 is the same as system 300, shown in FIGS. 3–6, except for the addition of a third diode 705, a fourth diode 710, and a sixth switch 725. Fourth switch 340 and fifth switch 345 of system 300 are implemented in system 700 with diodes. Third diode 705 is coupled in parallel across second switch 330, and fourth diode 710 is coupled in parallel across third switch 335. Sixth switch 725 is coupled between the anode of first capacitor 305 and the cathode of second capacitor 310. Thus, when second switch 330 is closed, and first switch 325, third switch 335, fourth switch 340, fifth switch 345, and sixth switch 725 are open, second high voltage transformer 320 completes charging second capacitor 310 to a desired voltage. Once second capacitor 310 is fully charged, capacitor reformation is complete and the charge on second capacitor 310 can be dumped into a dummy load (not shown) or allowed to bleed off.

As described above in conjunction with FIG. 2, an ICD can deliver electrical therapy to a patient, such as a defibrillation shock. To generate a shocking pulse, the ICD must quickly charge its high voltage capacitors. For example, in system 700 shown in FIG. 7, first and second capacitor 305 and 310 can be simultaneously charged in preparation for delivering a shock when first and second switch 325 and 330 are closed, and third switch 335, fourth switch 340, fifth switch 345, and sixth switch 725 are open. The high voltage capacitors of an ICD are typically coupled in series to deliver a shock. Thus, sixth switch 725 of system 700 provides a mechanism for switching first and second capacitor 305 and 310 from an essentially parallel configuration (i.e., sixth switch 725 is open) during capacitor reformation to an essentially series configuration (i.e., sixth switch 725 is closed) for delivering a shock.

Many different devices can be used to implement the switches of example systems 300 and 700. The choice of switching device depends on the means of activating the device (i.e., voltage or current) and whether the high voltage circuitry is grounded or floating. For the switches shown in FIGS. 3–7, the additional circuitry used to activate the switches would be apparent to a person skilled in the art.

For example, first switch 325, second switch 330, and third switch 335 can each be implemented with a bipolar junction transistor (BJT), field effect transistor (FET), or thyristor. In system 700, second switch 330 and third switch 335 can each be implemented with an insulated gate bipolar transistor (IGBT) or FET, so that third diode 705 and fourth diode 710 can be incorporated into the respective IGBT or FET structures. Thus, third diode 705 and fourth diode 710 would not be discrete devices (as shown in FIG. 7), thereby reducing the size and complexity of the circuit. Fourth switch 340 and fifth switch 345 can each be implemented with an IGBT, FET, or diode (as shown in FIG. 7). Implementing fourth and fifth switches 340 and 345 with diodes is less efficient but reduces the complexity and size of the circuit.

First and second high voltage transformers 315 and 320 of example systems 300 and 700 can be implemented as two separate transformers. Alternatively, first and second high voltage transformers 315 and 320 can be implemented as two secondaries of the same transformer. As would be apparent to a person skilled in the art, the primary windings of the transformer would be coupled to the ICD battery.

Figure 8:
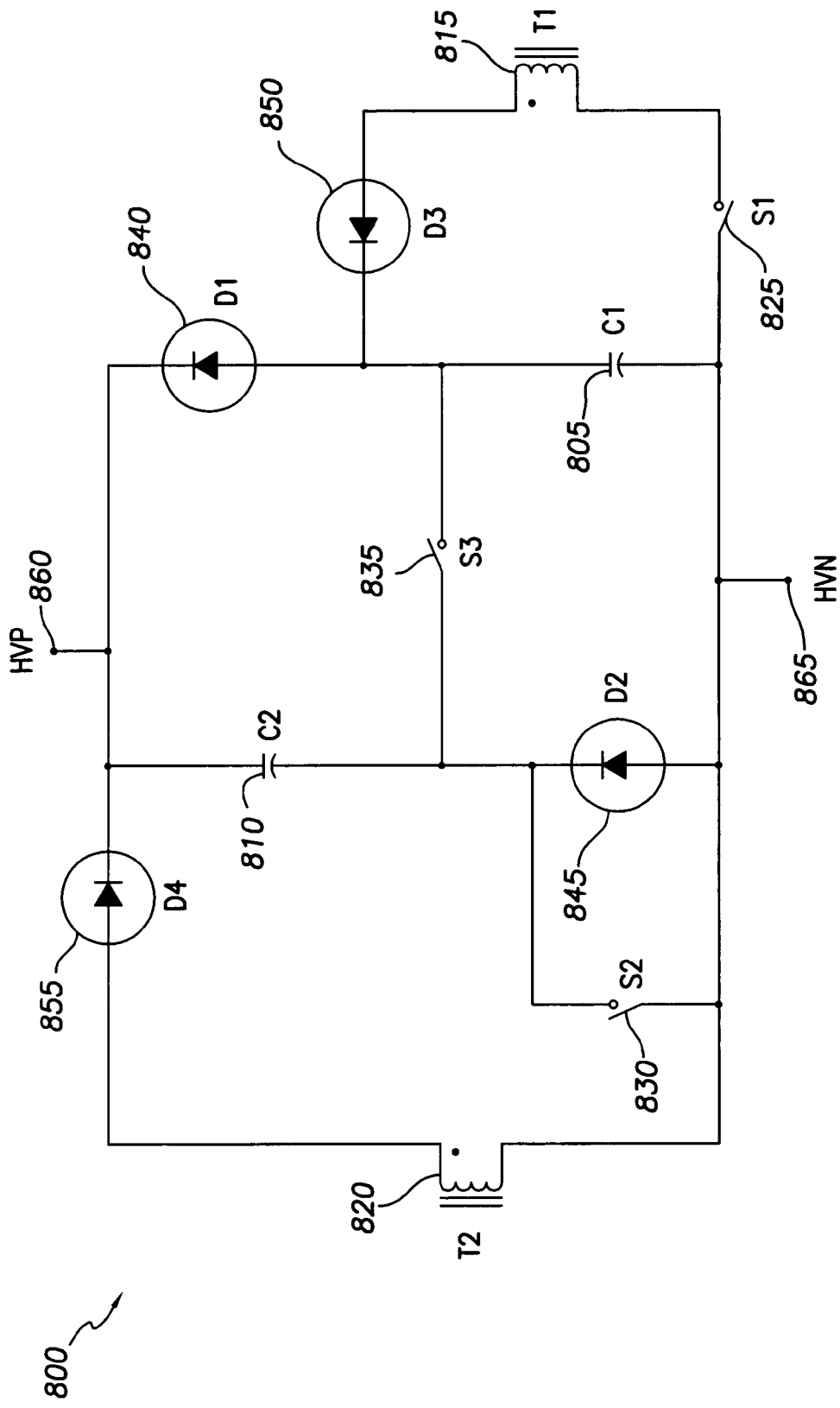
FIGS. 8–11 illustrate an example system for sharing energy between two capacitors to increase capacitor reformation efficiency in an ICD.

FIGS. 8–11 illustrate an example system 800 for sharing energy from one high voltage capacitor with another high voltage capacitor to increase capacitor reformation efficiency in an ICD. As shown in FIG. 8, system 800 includes first and second capacitors 805 and 810, and first and second high voltage transformers (i.e. transformers secondary windings) 815 and 820. System 800 further includes a first switch 825, a second switch 830, and a third switch 835, in addition to a first diode 840, a second diode 845, a third diode 850, and a fourth diode 855.

As shown in FIG. 8, first switch 825 is coupled between first high voltage transformer 815 and a cathode of first capacitor 805, while second switch 830 is coupled between a cathode of second capacitor 810 and the cathode of first capacitor 805. Third switch 835 is coupled between the cathode of second capacitor 810 and the anode of first capacitor 805. First diode 840 has the anode coupled to the anode of first capacitor 805 and the cathode coupled to the anode of second capacitor 810. Second diode 845 is coupled in parallel across second switch 830. Third diode 850 has the anode coupled to first high voltage transformer 815 and the cathode coupled to the anode of first capacitor 805. Fourth diode 855 has the anode coupled to second high voltage transformer 820 and the cathode coupled to the anode of second capacitor 810. The anode of second capacitor 810 is coupled to a positive high voltage bus 860, and the cathode of first capacitor 805 is coupled to a negative high voltage bus 865.

Figure 9:
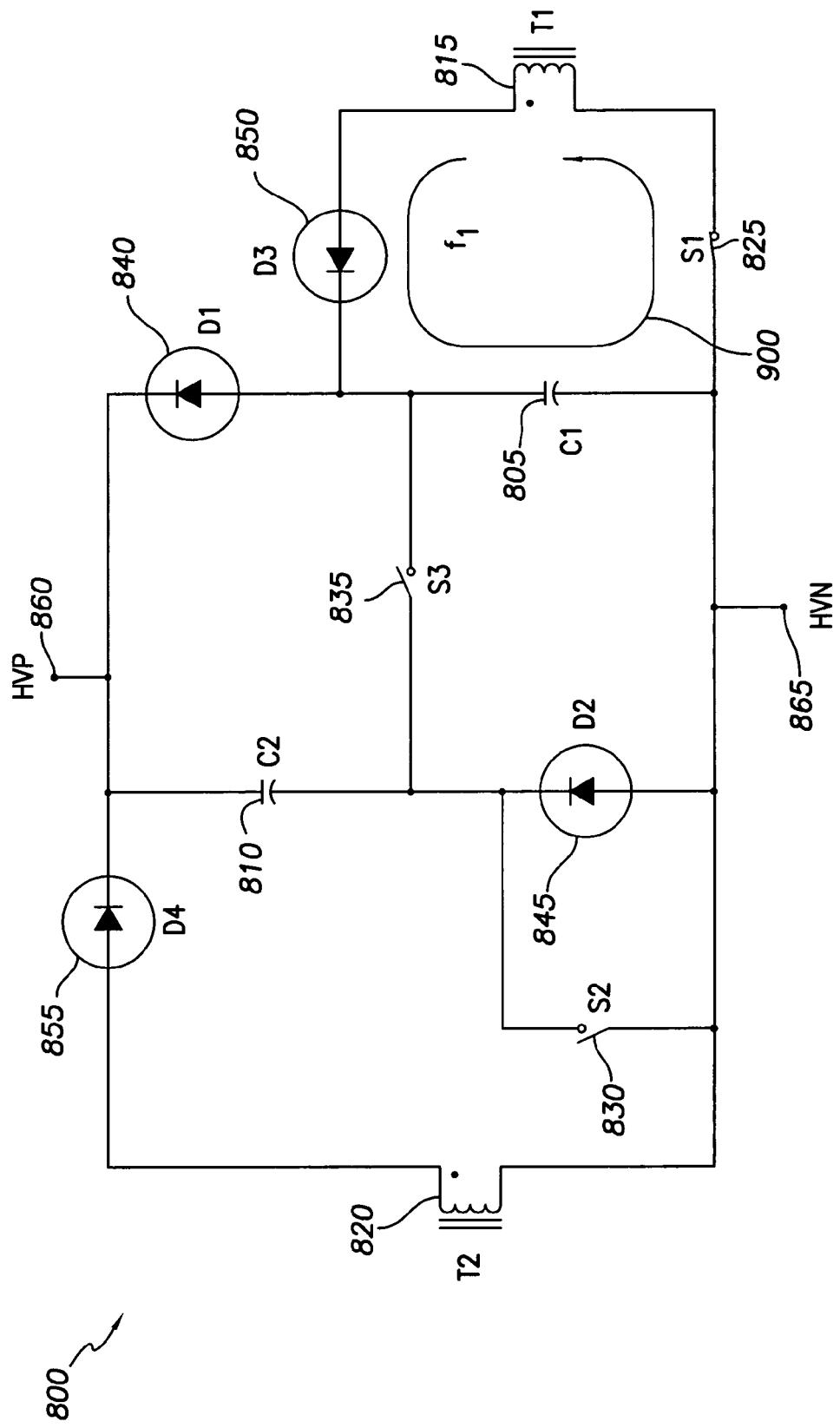

FIG. 9 illustrates a current path 900 that exists when first switch 825 is closed, and second switch 830 and third switch 835 are open. When the switches of system 800 are configured as shown in FIG. 9, current flows from first high voltage transformer 815, through third diode 850, and charges first capacitor 805 to a desired voltage.

Figure 10:
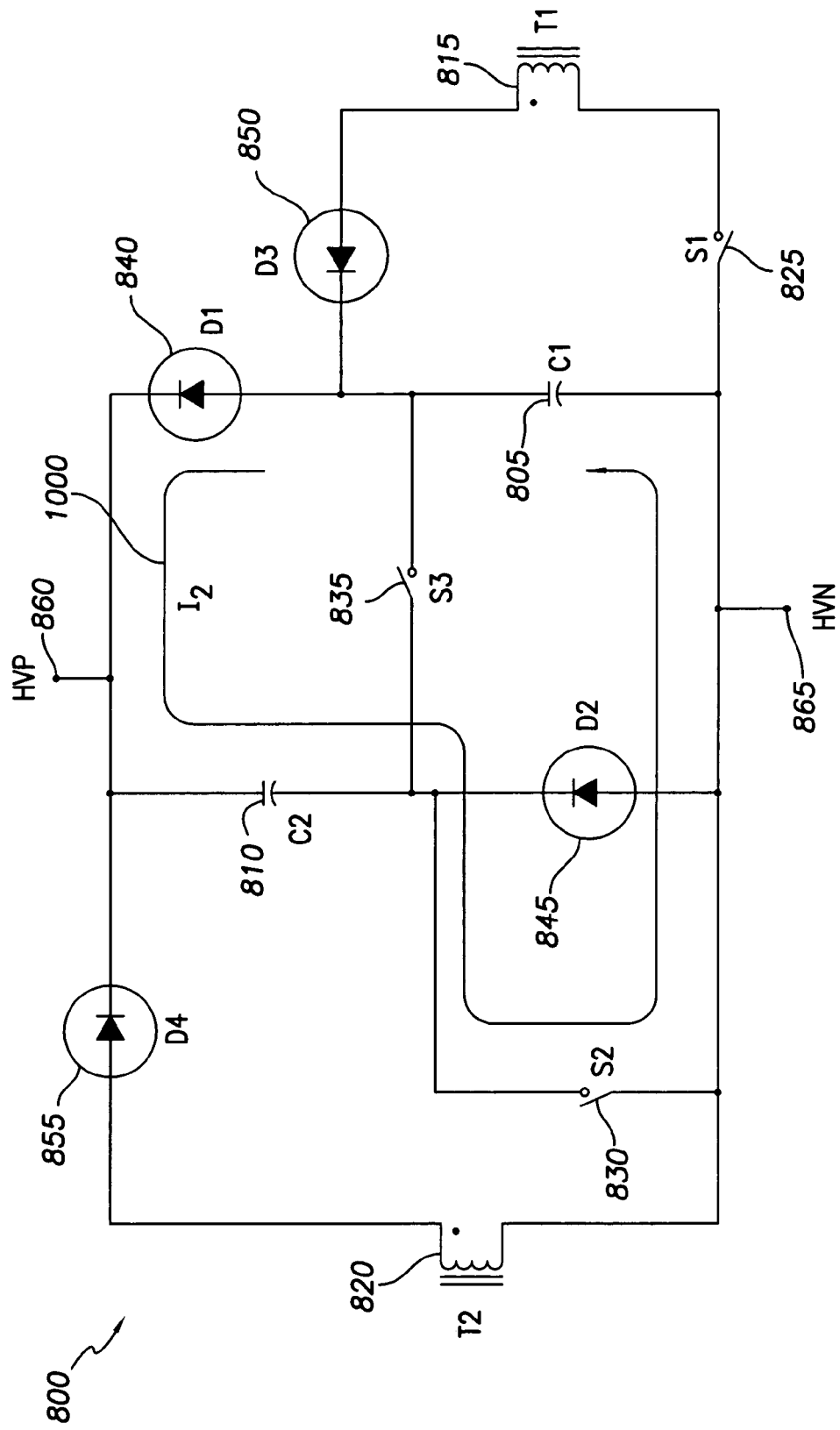

FIG. 10 illustrates a current path 1000 that exists when second switch 830 is closed, and first switch 825 and third switch 835 are open. When the switches of system 800 are configured as shown in FIG. 10, first capacitor 805 and second capacitor 810 are coupled in parallel. When two capacitors are placed in parallel, the voltage is distributed between them such that charge is conserved. Thus, in FIG. 10, current flows from first capacitor 805, through first diode 840, and is shared with second capacitor 810 until the charge between first and second capacitor 805 and 810 is balanced/equalized. The energy from first capacitor 805 partially charges second capacitor 810.

Figure 11:
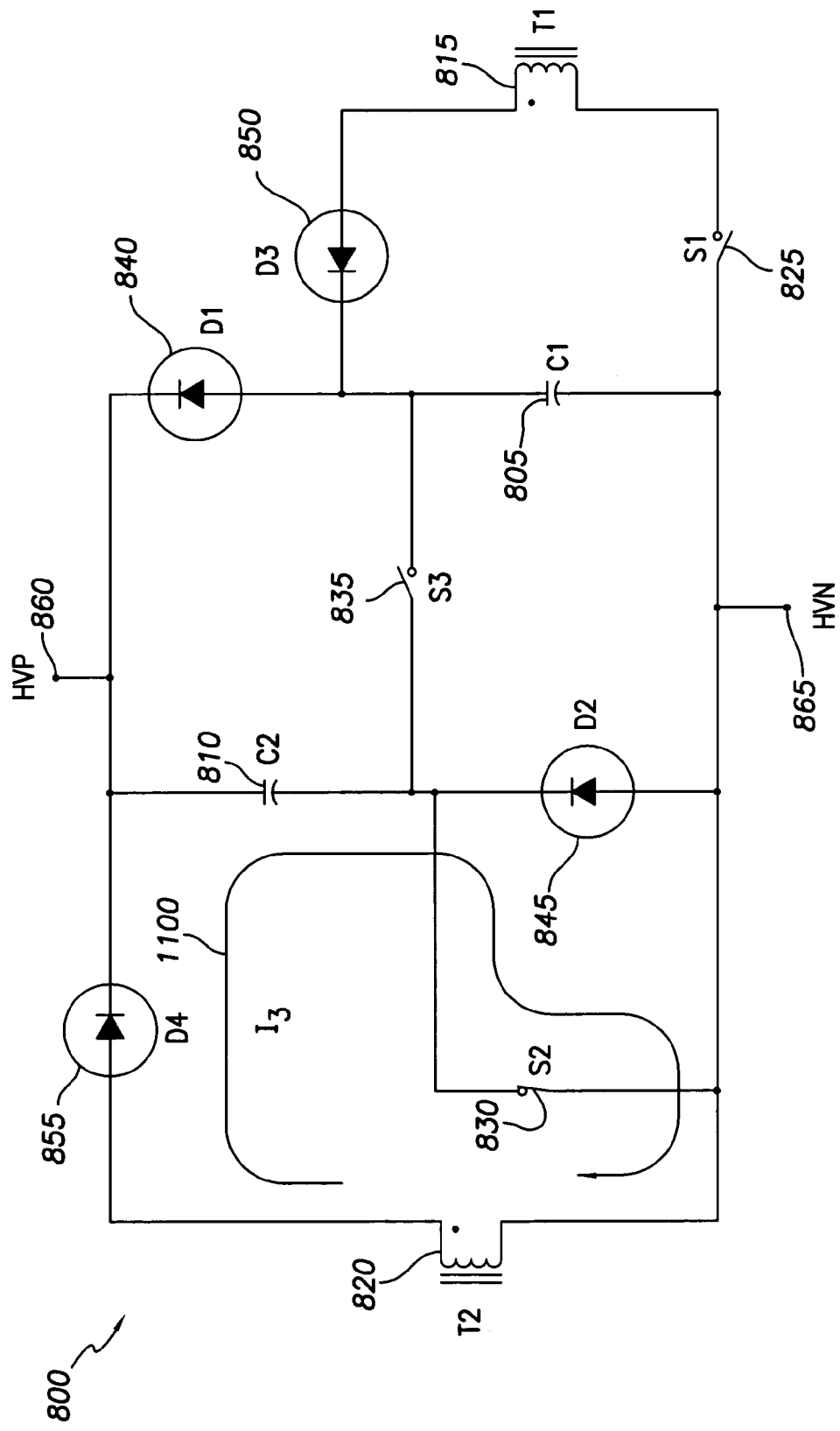

FIG. 11 illustrates a switching configuration for system 800 for completing charging second capacitor 810 from partially to fully charged. As shown in FIG. 11, a current path 1100 exists when second switch 830 is closed, and first switch 825 and third switch 835 are open. Current flows from second high voltage transformer 820, through fourth diode 855, and completes charging second capacitor 810 to a desired voltage. Once second capacitor 810 is fully charged, capacitor reformation is complete and the charge on second capacitor 810 can be dumped into a dummy load (not shown) or allowed to bleed off.

Like system 700 described above, system 800 can be configured to deliver electrical therapy. For example, when first and second switch 825 and 830 are closed, and third switch 835 is open, first and second capacitor 805 and 810 can be simultaneously charged in preparation for delivering a shock. Also, like sixth switch 725 of system 700 described above, third switch 835 of system 800 provides a mechanism for switching first and second capacitor 805 and 810 from a parallel configuration (i.e., third switch 835 is open) during capacitor reformation to a series configuration (i.e., third switch 835 is closed) for delivering a shock.

Many different devices can be used to implement the switches of system 800. As described above in conjunction with systems 300 and 700, the choice of switching device depends on the means of activating the device (i.e., voltage or current) and whether the high voltage circuitry is grounded or floating. For the switches shown in FIGS. 8–11, the additional circuitry used to activate the switches would be apparent to a person skilled in the art.

For example, first switch 825 can be implemented with a PNP BJT, P-channel FET, or silicon controlled rectifier (SCR) (or triac) configured with the anode coupled to negative high voltage bus 865. Similarly, second switch 830 can be implemented with an NPN BJT, N-channel FET, IGBT, or an SCR (or triac) configured with the cathode coupled to negative high voltage bus 865.

While example systems 300, 700, and 800 have been described for ICDs having two high voltage capacitors, these systems can also be implemented for ICDs having more than two high voltage capacitors, as will be apparent to persons skilled in the relevant art(s) based on the teachings herein. In the example of an ICD with four high voltage capacitors, the first capacitor of systems 300, 700, and 800 can be implemented as two capacitors coupled in series, and the second capacitor of systems 300, 700, and 800 can be implemented as two capacitors coupled in series. Thus, systems 300, 700, and 800 can be used to transfer and/or share energy between the first two capacitors coupled in series and the second two capacitors coupled in series. In the example of an ICD with three high voltage capacitors, systems 300, 700, and 800 can be used to transfer and/or share energy between a first capacitor and a second capacitor, and between the second capacitor and a third capacitor.

Methods for Increasing Capacitor Reformation Efficiency in an ICD

FIGS. 12–17 show process flowcharts providing steps for increasing capacitor reformation efficiency in an ICD. The steps of FIGS. 12–17 do not necessarily have to occur in the order shown, as will be apparent to persons skilled in the relevant art(s) based on the teachings herein. Other operational and structural embodiments will be apparent to persons skilled in the relevant art(s) based on the following discussion. These steps are described in detail below.

Figure 12:
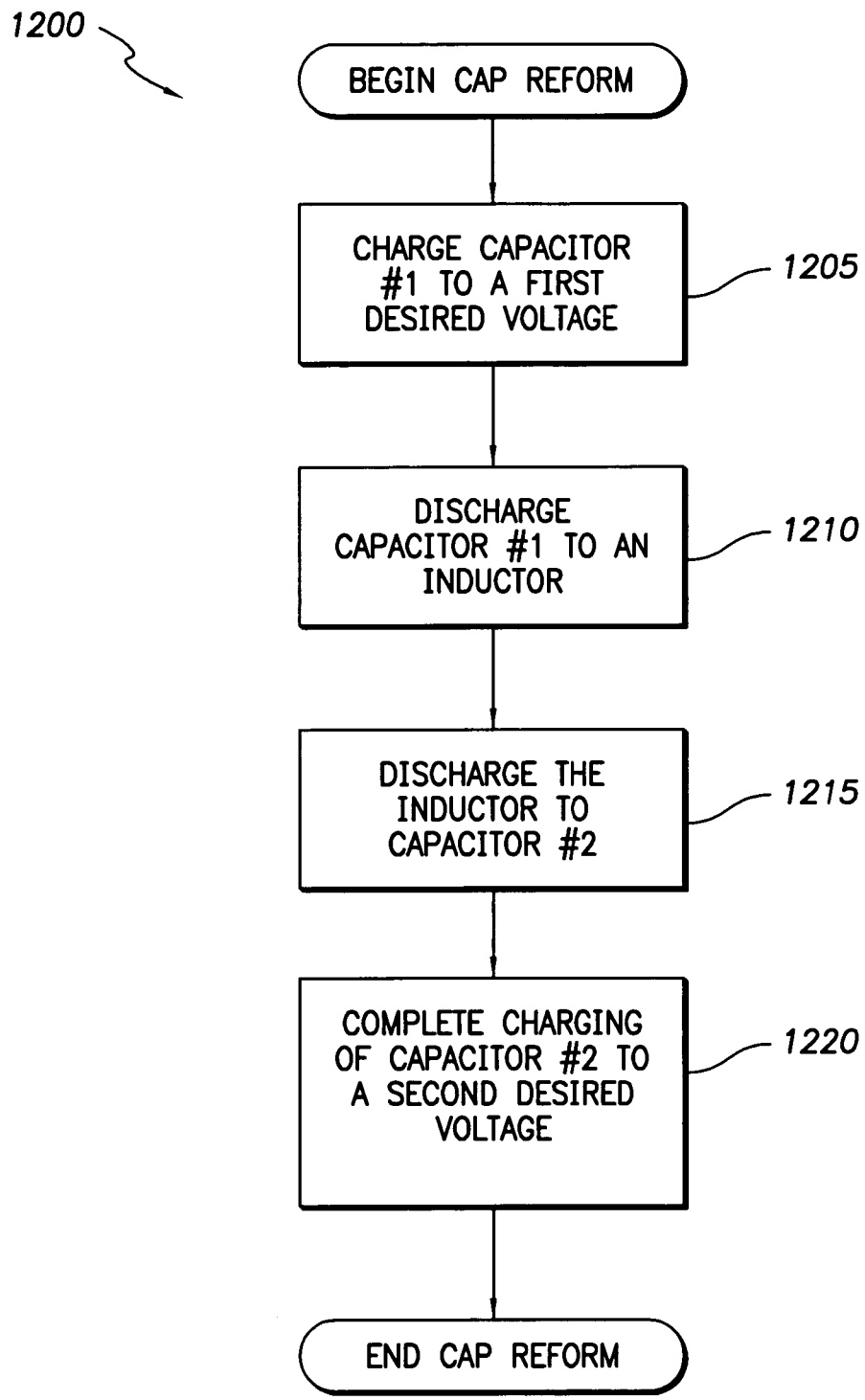
FIG. 12 shows a high level process flowchart providing steps for transferring energy from one capacitor to another capacitor through an inductor to increase capacitor reformation efficiency in an ICD.

FIG. 12 shows a high-level process flowchart 1200 providing steps for transferring energy from one high voltage capacitor to another high voltage capacitor using an inductor to increase capacitor reformation efficiency in an ICD. In step 1205, a first capacitor is fully charged to a first desired voltage, and in step 1210, the first capacitor is discharged to an inductor. A transformer or a secondary of a transformer, such as second high voltage transformer 320 of FIG. 5A, can serve as the inductor. In step 1215, the inductor is discharged to a second capacitor. Thus, the charge stored on the first capacitor is transferred to the second capacitor through the inductor. Steps 1210 and 1215 can be repeated until all of the charge stored on the first capacitor during step 1205 is transferred through the inductor to the second capacitor. Because the energy transfer from the first capacitor to the second capacitor through the inductor is not ideal, the second capacitor is only partially charged following step 1215. Thus, in step 1220, the second capacitor is fully charged to a second desired voltage to complete capacitor reformation.

Figure 13:
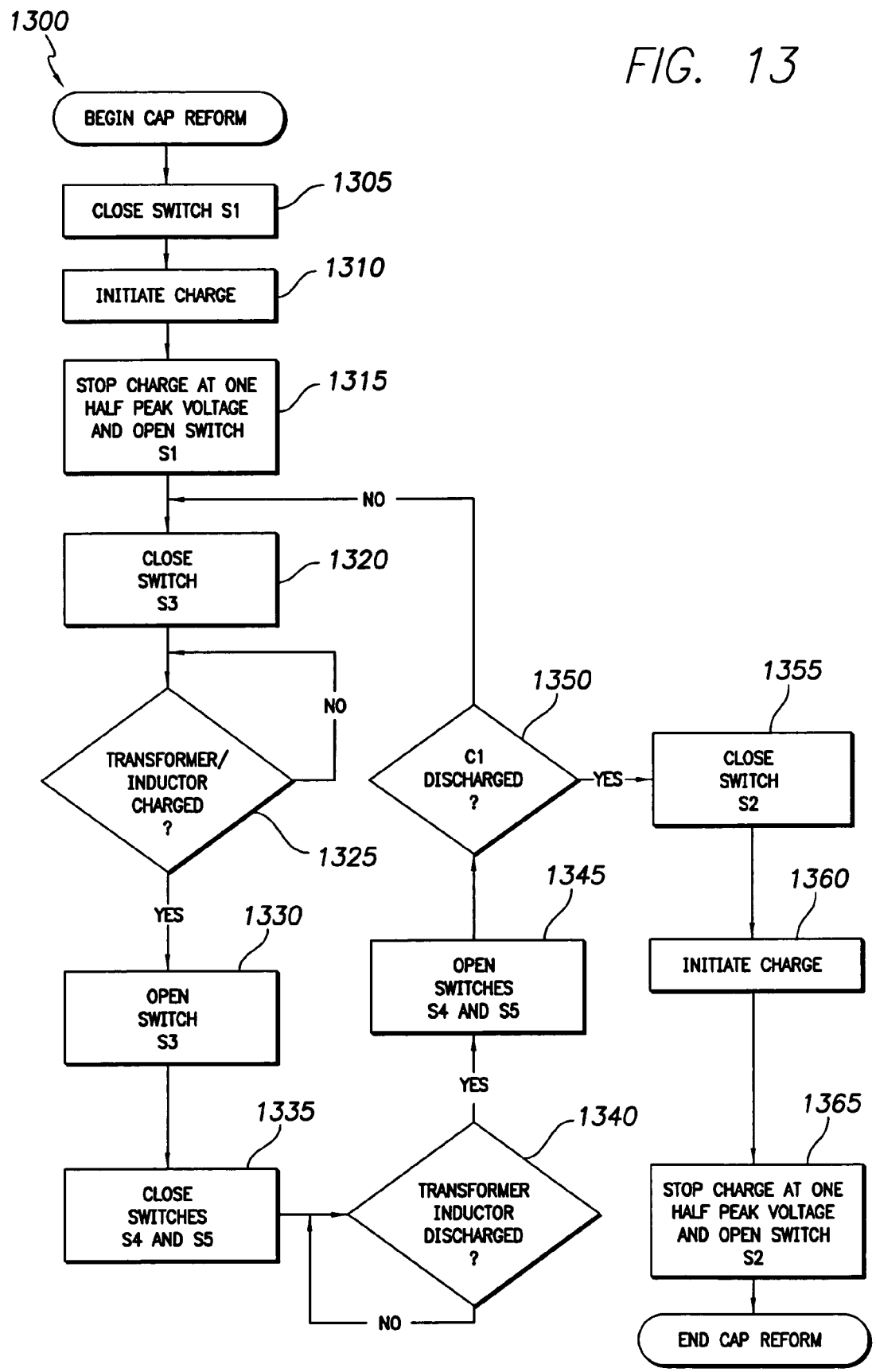
FIG. 13 shows a detailed process flowchart providing steps for increasing capacitor reformation efficiency in an ICD according to the example systems of FIGS. 3–7.

FIG. 13 shows a detailed process flowchart for transferring energy from a one high voltage capacitor to another high voltage capacitor using an inductor to increase capacitor reformation efficiency in an ICD, according to systems 300 and 700 of FIGS. 3–7. In step 1305, a first switch is closed, and in step 1310, charging of a first capacitor is initiated. For example, as shown in FIG. 4, the first capacitor can be first capacitor 305 and the first switch can be first switch 325. A transformer or a secondary of a transformer, such as first high voltage transformer 315 of FIG. 4, can charge the first capacitor.

In step 1315, after the first capacitor is charged to a desired voltage (e.g., one half peak voltage), charging stops and the first switch is opened. In step 1320, a third switch is closed, and in step 1325 an inductor (e.g., a transformer or a secondary of a transformer serving as an inductor) is charged. When the third switch is closed, the charge stored on the first capacitor is transferred to the inductor. For example, as shown in FIG. 5A, the first capacitor can be first capacitor 305, the third switch can be third switch 335, and the inductor can be second high voltage transformer 320.

In step 1330, the third switch is opened after the inductor is fully charged. In step 1335, a fourth switch and a fifth switch are closed, and in step 1340, the inductor is discharged to the second capacitor. When the fourth and fifth switches are closed, the charge stored in the inductor is transferred to the second capacitor until the inductor is discharged. For example, as shown in FIG. 6A, the fourth switch can be fourth switch 340, the fifth switch can be fifth switch 345, the inductor can be second high voltage transformer 320, and the second capacitor can be second capacitor 310.

In step 1345, the fourth switch and the fifth switch are opened after the inductor is discharged. In step 1350, if the first capacitor is not completely discharged, then steps 1320 through 1345 are repeated until all of the charge on the first capacitor is transferred to the second capacitor through the inductor.

In step 1355, a second switch is closed after the first capacitor is completely discharged, and in step 1360, charging of the second capacitor is initiated. For example, as shown in FIG. 7, the second switch can be second switch 330 and the second capacitor can be second capacitor 310. A transformer or a secondary of a transformer, such as second high voltage transformer 320 of FIG. 7, can charge the second capacitor.

In step 1365, after the second capacitor is charged to a desired voltage (e.g., one half peak voltage), charging stops and the second switch is opened.

Figure 14:
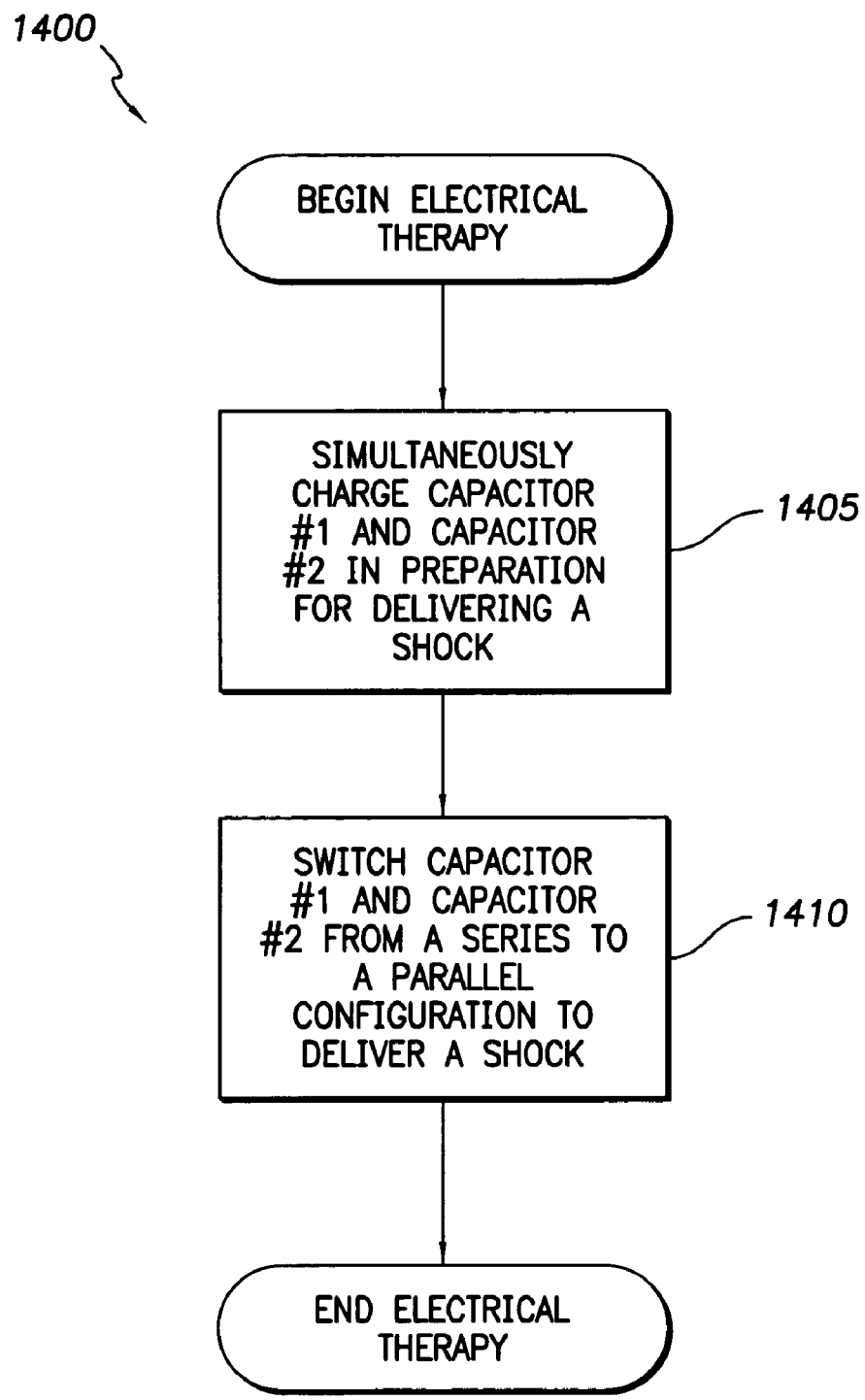
FIG. 14 shows a process flowchart providing additional steps for delivering electrical therapy.

The processes shown in FIGS. 12 and 13 apply during capacitor reformation, while FIG. 14 shows a process flowchart 1400 providing additional steps for delivering electrical therapy. In step 1405, first and second capacitors are simultaneously charged to desired voltages in preparation for delivering a shock. For example, when first switch 325 and second switch 330 of system 700 of FIG. 7 are closed, and the remaining switches of system 700 are open, first capacitor 305 and second capacitor 310 can be simultaneously charged in preparation for delivering a shock.

In step 1410, the first and second capacitors are switched from a parallel configuration during capacitor reformation to a series configuration for delivering a shock. For example, as shown in FIG. 7, when sixth switch 725 is open, first and second capacitors 305 and 310 are coupled in an essentially parallel configuration, and when sixth switch 725 is closed, first and second capacitors 305 and 310 are coupled in an essentially series configuration.

FIG. 15 shows a process flowchart 1500 providing steps for sharing energy between first and second high voltage capacitors to increase capacitor reformation efficiency in an ICD, according to system 800 of FIGS. 8–11. In step 1505, a first switch is closed, and in step 1510, charging of a first capacitor is initiated. For example, as shown in FIG. 9, the first switch can be first switch 825 and the first capacitor can be first capacitor 805. A transformer or a secondary of a transformer such as first high voltage transformer 815 of FIG. 9, can charge the first capacitor.

In step 1520, when the first capacitor is fully charged (e.g., to one half peak voltage), the first switch is opened to stop charging the first capacitor. In step 1525, a second switch is closed so that charge from the first capacitor is shared with the second capacitor. When two capacitors are placed in parallel, the voltage is distributed between them such that charge is conserved. For example, as shown in FIG. 10, the second switch can be second switch 830 and the second capacitor can be second capacitor 810.

In step 1530, charge is shared between the first and second capacitor until the charge on both capacitors is balanced/equalized. After step 1530, the second capacitor is partially charged. Thus, in step 1535, completing charging of the second capacitor is initiated. A transformer or a secondary of a transformer can charge the second capacitor. For example, as shown in FIG. 11, when second switch 830 is closed, second high voltage transformer 820 can charge second capacitor 810.

In step 1540, when the second capacitor is fully charged (e.g., to one half peak voltage), the second switch is opened to stop charging the second capacitor and capacitor reformation is complete.

FIG. 16 shows a high level process flowchart 1600 providing steps for sharing energy, and for transferring energy using an inductor to increase capacitor reformation efficiency in an ICD. In step 1605, a first capacitor is charged to a desired voltage. In step 1610, the charge on the first capacitor is shared with a second capacitor until the charge on both capacitors is balanced/equalized. In step 1615, the remaining charge on the first capacitor is transferred to an inductor. Then, in step 1620, the inductor is discharged to the second capacitor to fully charge the second capacitor to a desired voltage and complete capacitor reformation.

FIG. 17 shows a detailed process flowchart 1700 providing steps for sharing energy, and for transferring energy using an inductor to increase capacitor reformation efficiency in an ICD, according to the system of FIGS. 3–7. In step 1705, a first switch is closed and charging of a first capacitor is initiated. For example, as shown in FIG. 4, the first switch can be first switch 325 and the first capacitor can be first capacitor 305. A transformer or a secondary of a transformer, such as first high voltage transformer 315 of FIG. 4, can charge the first capacitor to a desired voltage.

In step 1710, after the first capacitor is fully charged (e.g., to one half peak voltage), the first switch is opened to stop charging of the first capacitor. In step 1715, a second switch is closed so that charge on the first capacitor can be shared with a second capacitor. When two capacitors are placed in parallel, the voltage is distributed between them such that charge is conserved. For example, as shown in FIG. 3, the second switch can be second switch 330 and the second capacitor can be second capacitor 310, such that when second switch 330 is closed and the remaining switches of system 300 are open, first capacitor 305 and second capacitor 310 are coupled in a parallel configuration.

In step 1720, charge is shared between the first and second capacitor until the charge on both capacitors is balanced/equalized. After step 1720, the second capacitor is partially charged and an amount of charge remains on the first capacitor. Thus, in step 1725, the second switch is opened and a third switch is closed so that the remaining charge on the first capacitor can be transferred to an inductor. For example, as shown in FIG. 5A, the third switch can be third switch 335, and the inductor can be second high voltage transformer 320.

In step 1730, charge is transferred from the first capacitor to the inductor until the first capacitor is discharged. In step 1735, the third switch is opened and a fourth switch and a fifth switch are closed so that the charge stored in the inductor can be transferred to the second capacitor. For example, as shown in FIG. 6A, the fourth switch can be fourth switch 340, the fifth switch can be fifth switch 345, and the inductor can be second high voltage transformer 320.

In step 1740, charge is transferred from the inductor to the second capacitor until the inductor is discharged. After step 1740, the second capacitor is partially charged because the charge transfer between the first and second capacitors is not ideal. Thus, in step 1745, the fourth and fifth switches are opened, the second switch is closed, and completing charging of the second capacitor is initiated. A transformer or a secondary of a transformer, such as second high voltage transformer 320 of FIG. 7, can charge the second capacitor to a desired voltage (e.g., to one half peak voltage). When the second capacitor is fully charged, capacitor reformation is complete.

Increased Capacitor Reformation Efficiency in an ICD

The methods and systems presented herein for increasing capacitor reformation efficiency in an ICD are advantageous because the energy used to reform a first capacitor is not "wasted" and is used to at least partially charge a second capacitor. Thus, because less energy is required to fully charge the second capacitor from a partially charged state than from an uncharged state, capacitor reformation efficiency increases, thereby increasing the longevity of the ICD.

For example, assume that when an ICD battery charges both a first and a second capacitor from uncharged to fully charged, 100% charge from the battery is required so a 0% energy reduction is realized. Thus, when systems 300 and 700 and methods 1200, 1300, 1600, and 1700 are implemented, a 50% energy reduction would ideally be realized. Instead of charging both capacitors to full energy, the battery need only charge the first capacitor to full energy. The energy from the first capacitor is transferred to the second capacitor, thereby charging the second capacitor to full energy and requiring 0% charge from the battery. Thus, assuming the switches and inductor of the systems and methods are lossless, 50% charge from the battery would be required to form both capacitors. Because the systems and methods are not ideal, however, about 57.5% charge from the battery is required to form both capacitors.

FIG. 18 shows a plot of the increased longevity of an example ICD as a function of the percentage of charge required from the battery for periodic capacitor reformation, assuming no shocks are delivered (i.e., best case scenario). The increased longevity is mainly dependent upon the type of battery and capacitor used. In the example of FIG. 18, for 100% charge (i.e., the battery must fully charge both capacitors), the expected longevity of the ICD is about 6.1 years for quarterly capacitor reformation and about 4.6 years for monthly capacitor reformation.

As described above, to form both capacitors, systems 300 and 700 and methods 1200, 1300, 1600, and 1700 require about 57.5% charge from the battery, which corresponds to an energy reduction of about 42.5%. Thus, in the example of FIG. 18, the expected longevity for the ICD would increase to about 7.1 years for quarterly capacitor reformation and to about 5.9 years for monthly capacitor reformation from 6.1 years and 4.6 years, respectively.

For system 800 and method 1500, a 12.5% energy reduction is expected. For example, the amount of energy saved by transferring the charge from a first capacitor to a second capacitor during capacitor reformation can be calculated as follows. The energy contained in a charged capacitor is given by:

$$E_1 = \frac{1}{2}CV^2 \quad (1)$$

where E1 is the energy in Joules, C is the capacitance in Farads, V is the voltage in Volts. The charge on the capacitor is given by:

$$Q = CV \quad (2)$$

When two capacitors are placed in parallel, the voltage is distributed between them such that charge is conserved. Thus, when capacitors of equal value, one being charged and the other having no charge, are placed in parallel, the shared voltage is given by:

$$V_s = \frac{V}{2} \quad (3)$$

where $V_S$ is the shared voltage in Volts and V is the voltage on the charged capacitor in Volts.

The energy required to charge the second capacitor to a specified voltage is given by:

$$E_2 = \frac{1}{2}C(V^2 - V_S^2) \quad (4)$$

Thus, the total energy used to charge the first and the second capacitors individually to full voltage is given by:

$$E_{REFORM} = E_1 + E_2 = \frac{7}{8}CV^2 \quad (5)$$

While the total energy used to reform the first and second capacitors at the same time is given by:

$$E_{TOTAL} = 2E_1 = CV^2 \quad (6)$$

Therefore, the energy savings using the capacitor switching scheme of system 800 and method 1500 is given by:

$$EnergySavings = \frac{E_{TOTAL} - E_{REFORM}}{E_{TOTAL}} = 12.5\% \quad (7)$$

Thus, in the example of FIG. 18, the expected longevity for the ICD would increase to about 6.3 years for quarterly capacitor reformation and to about 4.9 years for monthly capacitor reformation.

CONCLUSION

Example methods and systems for increasing capacitor reformation efficiency in an ICD have been described herein. As noted elsewhere, these example embodiments have been described for illustrative purposes only, and are not limiting. Other embodiments are possible and are covered by the methods and systems described herein. Such embodiments will be apparent to persons skilled in the relevant art(s) based on the teachings contained herein. Thus, the breadth and scope of the methods and systems described herein should not be limited by any of the above-described exemplary embodiments, but should be defined only in accordance with the following claims and their equivalents.

What is claimed is:

1. In an implantable cardiac defibrillator (ICD) having first and second charge-storage capacitors requiring periodic reformation by charging the capacitors to a desired voltage, a method for increased capacitor reformation efficiency, comprising:
   (a) charging the first capacitor to a first desired voltage;
   (b) discharging the first capacitor to an inductor;
   (c) discharging the inductor to the second capacitor, whereby the second capacitor is at least partially charged by the inductor; and
   (d) completing charging of the second capacitor to a second desired voltage.

2. The method of claim 1, further comprising:
   repeating steps (b) and (c) until a desired amount of charge is transferred from the first capacitor to the second capacitor.

3. The method of claim 1, wherein the first and second desired voltages are the same voltage.

4. The method of claim 1, further comprising coupling the first capacitor in a series configuration with the second capacitor in preparation to deliver electrical therapy.

5. The method of claim 1, further comprising a step between steps (a) and (b) of coupling the first capacitor in a parallel configuration with the second capacitor so that the first capacitor partially charges the second capacitor.

6. The method of claim 1, wherein step (a) comprises:
closing a first switch coupled between a first high voltage transformer and a cathode of the first capacitor;
opening a second switch coupled between a cathode of the second capacitor and the cathode of the first capacitor;
opening a third switch coupled between a second high voltage transformer and the cathode of the first capacitor;
opening a fourth switch coupled between the second high voltage transformer and an anode of the second capacitor; and
opening a fifth switch coupled between the second high voltage transformer and the cathode of the second capacitor.

7. The method of claim 6, wherein step (b) comprises:
opening the first switch; and
closing the third switch.

8. The method of claim 7, wherein step (c) comprises:
opening the third switch; and
closing the fourth and fifth switches.

9. The method of claim 8, wherein step (d) comprises:
opening the fourth and fifth switches; and
closing the second and third switches.

10. The method of claim 6, further comprising the steps of:
during reformation of the first and second capacitors, opening a sixth switch coupled between the cathode of the second capacitor and an anode of said first capacitor; and
in preparation to deliver electrical therapy, closing the second switch and charging the first and second capacitors simultaneously.

11. The method of claim 10, further comprising:
to deliver electrical therapy, opening the first and second switches and closing the sixth switch.

12. The method of claim 1, wherein the ICD has at least one additional charge-storage capacitor requiring periodic reformation, the method further comprising:
repeating steps (b) through (d) until each additional capacitor is charged to a respective desired voltage by transferring charge from a previously charged capacitor through the inductor.

13. In an implantable cardiac defibrillator (ICD) having a plurality of charge-storage capacitors, a system for increased capacitor reformation efficiency, comprising:
means for charging a first capacitor to a first desired voltage;
means for transferring the charge from the first capacitor to an inductor;
means for transferring the charge from the inductor to a second capacitor, whereby the second capacitor is at least partially charged by the inductor; and
means for completing charging of the second capacitor to a second desired voltage.

14. The system of claim 13, wherein said means for charging the first capacitor comprises:
switching means that directs charge from a first high voltage transformer to the first capacitor.

15. The system of claim 13, wherein said means for transferring the charge from the first capacitor comprises:
switching means that directs the charge from the first capacitor to a second high voltage transformer, wherein the second high voltage transformer serves as the inductor.

16. The system of claim 15, wherein said means for transferring the charge from the inductor comprises:
switching means that directs charge from the second high voltage transformer to the second capacitor.

17. The system of claim 16, wherein said means for completing charging of the second capacitor comprises:
switching means that directs charge from the second high voltage transformer to the second capacitor.

18. The system of claim 13, further comprising:
means for coupling the first capacitor in a parallel configuration with the second capacitor prior to transferring the charge from the first capacitor to the inductor so that the first capacitor partially charges the second capacitor.

19. In an implantable cardiac defibrillator (ICD) having first and second charge-storage capacitors, a circuit for increased capacitor reformation efficiency, comprising:
a first switch coupled between a cathode of the first capacitor and a first high voltage transformer;
a second switch coupled between the cathode of the first capacitor and a cathode of the second capacitor;
a third switch coupled between a second high voltage transformer and the cathode of the first capacitor;
a fourth switch coupled between the second high voltage transformer and an anode of the second capacitor;
a fifth switch coupled between the second high voltage transformer and the cathode of the second capacitor;
a first diode having an anode coupled to an anode of the first capacitor and a cathode coupled to the anode of the second capacitor; and
a second diode having an anode coupled to the first high voltage transformer and a cathode coupled to the anode of the first capacitor,
wherein the first high voltage transformer charges the first capacitor to a desired voltage when said first switch is closed and said second, third, fourth and fifth switches are open;
wherein the first capacitor discharges to the second high voltage transformer when said third switch is closed and said first, second, fourth, and fifth switches are open; and
wherein the second high voltage transformer discharges to the second capacitor when said fourth and fifth switches are closed and said first, second, and third switches are open, whereby the second high voltage transformer at least partially charges the second capacitor.

20. The circuit of claim 19, further comprising:
third and fourth diodes coupled in parallel across said second and third switches, respectively, wherein the second high voltage transformer completes charging the second capacitor to a desired voltage when said second switch is closed and said first, third, fourth, and fifth switches are open.

* * * * *